United States Patent [19]
Curtiss et al.

[11] Patent Number: 5,814,467
[45] Date of Patent: *Sep. 29, 1998

[54] APO AI POLYPEPTIDES, DIAGNOSTIC METHODS AND SYSTEMS FOR QUANTIFYING APO AI, AND THERAPEUTIC METHODS

[75] Inventors: Linda K. Curtiss; Carole L. Banka, both of San Diego; David J. Bonnet, Poway; Richard S. Smith, Del Mar, all of Calif.

[73] Assignee: The Scripps Research Institute, La Jolla, Calif.

[ * ] Notice: The term of this patent shall not extend beyond the expiration date of Pat. No. 5,055,396.

[21] Appl. No.: 292,870

[22] Filed: Aug. 19, 1994

Related U.S. Application Data

[60] Division of Ser. No. 711,333, Jun. 6, 1991, abandoned, which is a continuation-in-part of Ser. No. 534,761, Jun. 7, 1990, abandoned.

[51] Int. Cl.$^6$ .................................................. G01N 33/53
[52] U.S. Cl. .......................... 435/7.9; 435/7.92; 435/975; 436/518; 530/388.25; 530/391.3; 530/811; 530/812
[58] Field of Search ..................................... 435/7.9, 70.2, 435/70.21, 975, 7.1, 7.92; 530/300, 387.1, 387.9, 388.1, 391.1, 388.25, 389.3, 391.3; 436/518

[56] References Cited

U.S. PATENT DOCUMENTS

| | | | |
|---|---|---|---|
| 3,654,090 | 4/1972 | Wilhelmus et al. | 435/518 |
| 4,677,057 | 6/1987 | Curtiss . | |
| 4,828,986 | 5/1989 | Smith et al. | 435/7 |
| 4,970,144 | 11/1990 | Fareed et al. | 435/5 |
| 5,055,396 | 10/1991 | Curtiss et al. | 435/7.93 |
| 5,126,240 | 6/1992 | Curtiss | 435/7.94 |

OTHER PUBLICATIONS

Campbell, A. M. in Laboratory Techniques in Biochemistry and Molecular Biology, vol. 23 Elsevier, Amsterdam©1991 pp. 1–49.

Curtiss et al, 260 (5), Mar. 10, 1986, pp. 2982–2993, *J. Biol. Chem.*

Curtiss et al, J. Biol. Chem, Sep. 25, 1988, 263 (27) pp. 13779–13785.

Marcovina et al, J. Lipid Res, 1990, 31:375–384.

Brewer et al., Biochem. Biophys. Res. Comm., 80:623–630 (1978).

Curtiss et al., "Immunochemical Heterogeneity of HDL" Proceeding of the Workshop in Lipoprotein Heterogeneity, Ed. by Lippel, National Institutes of Health Publication No. 87–2646, pp. 363–377 (1987).

Curtiss et al., "Biotechnology of Dyslipoproteinemias: Clinical Applications in Diagnosis and Control", Lenfant et al., eds, pp. 217–225, Raven Press, New York (1990).

Epand et al., J. Biol. Chem., 262:9389–9396 (1987).

Fukushima et al., *J. Biol. Chem.*, 255:10651–10657 (1980).

Hogle et al., *J. Lipid Res.*, 29:1221–1229 (1988).

Marcovina et al., *J. Lipid Res.*, 31:375–384 (1990).

Milthrop et al., Anterio., 6:285–296 (1986).

Niman et al., Proc. Natl. Acad. Sci. USA, 80:4949–4953 (1983).

Ponsin et al., *Biochem.*, 23:5337–5342 (1984).

Ponsin et al., *J. Biol. Chem.*, 261:9202–9205 (1986).

Pownall et al., *Biochim. Biophys. Acta.*, 793:149–156 (1984).

Sparrow et al., *Ann. N.Y. Acad. Sci.*, 384:187–208 (1980).

*Primary Examiner*—Paula K. Hutzell
*Assistant Examiner*—Patricia A. Duffy
*Attorney, Agent, or Firm*—Thomas Fitting; Emily Holmes

[57] ABSTRACT

The present invention describes an Apo AI polypeptide capable of immunologically mimicking an Apo AI epitope. The polypeptide is useful in diagnostic methods and systems for detecting Apo AI in vascular fluid samples, and for preparation of anti-Apo AI antibodies. In addition, the polypeptide is useful in therapeutic methods for increasing esterified cholesterol in a human patient.

18 Claims, 8 Drawing Sheets

APO AI POLYPEPTIDES, DIAGNOSTIC METHODS AND SYSTEMS FOR QUANTIFYING APO AI, AND THERAPEUTIC METHODS

CROSS REFERENCE TO RELATED APPLICATION

This is a divisional application of application Ser. No. 07/711,333, filed Jun. 6, 1991, now abandoned which is a Continuation-In-Part application of copending application Ser. No. 534,761, filed Jun. 7, 1990, now abandoned which applications are hereby incorporated by reference.

TECHNICAL FIELD

The present invention relates to diagnostic methods and polypeptides useful for immunologically determining the amount of Apo AI in a vascular fluid sample. In addition, the polypeptides are useful in therapeutic methods and compositions for increasing LCAT-mediated cholesterol esterification and the formation of cholesterol esters in a human patient.

BACKGROUND

Lipoproteins are the primary carriers of plasma cholesterol. They are micellar lipid-protein complexes (particles) having a surface film, comprised of one or more proteins associated with polar lipids, that surrounds a cholesterol-containing core. Lipoproteins were originally classified based on their buoyant densities as measured by ultracentrifugation. Accordingly, four major density classes have been recognized: chylomicrons, very low-density lipoproteins (VLDL), low-density lipoproteins LDL and high-density lipoproteins (HDL).

Many studies have now established an inverse correlation between plasma HDL cholesterol levels and risk of coronary artery disease (CAD). That is, elevated levels of plasma cholesterol found in HDL particles correlate with a reduced risk of CAD. See, for example, Goldbourt et al., *Int. J. Epidemiol.*, 15:51–55 (1986).

Similarly, many studies have now shown that plasma levels of apolipoprotein AI (Apo AI), the major protein component of HDL, are also inversely related to the risk of CAD. In addition, Weisweiler et al., *Clin. Chem.*, 27:348 (1981) have reported that knowledge of Apo AI levels may add to the predictive valve of HDL cholesterol.

Because of its inverse correlation with CAD, there has been an extensive amount of research into the structure and function of Apo AI in lipid metabolism. Functionally, Apo AI is now believed to mediate the removal of cholesterol from tissues.

Structurally, purified Apo AI has been described as containing a high proportion (55%) of alpha-helix, which increases to 70% when it is associated with phospholipids as in the HDL particle. The lipid binding properties of Apo AI appear to be a function of a series of tandemly repeated segments of 22 amino acid residues punctuated mostly by proline residues that are alpha-helical and amphophilic.

The amino acid residue sequence of Apo AI, determined by Edman degradation of cyanogen bromide-and trypsin-fragments of intact Apo AI, has been described by Brewer et al., *Biochem. Biophys. Res. Comm.*, 80:623–630 (1978). According to Brewer et al., cyanogen bromide (CNBr) cleavage of Apo AI produced four major fragments, designated CNBr1, CNBr2, CNBr3 and CNBr4, in order of their occurrence along the Apo AI sequence from amino-terminus to carboxy-terminus. Because it is of particular interest to the present invention, the amino acid residue sequence of the region of Apo AI from which CNBr2 and CNBr3 is produced is illustrated in FIG. 1.

Immunochemical characterization of native Apo AI, i.e., Apo AI as it is found on HDL particles, has been problematical because it is antigenically heterogeneous and unstable. The antigenic heterogeneity of Apo AI appears to be the result of some epitopes being masked by lipids in the intact HDL or the antibody-binding ability of some epitopes being dependent on conformations of Apo AI as affected by lipids or other HDL associated proteins. The antigenic instability of Apo AI, as manifest by its changing immunoreactivity over time with defined antisera, appears to be due to such phenomena as self association and deamidation, both of which have been shown to occur in vitro. See Curtiss et al., Proceeding of the Workshop on Lipoprotein Heterogeneity, Ed. by Lippel, National Institutes of Health Publication No. 87-2646, P. 363–377 (1987). According to Milthorp et al., *Arterio.*, 6:285–296 (1986), the effects of storage and NaOH treatment on native Apo AI immunoreactivity are similar but not analogous, suggesting that while loss of Apo AI immunoreactivity during storage is due in large part to deamidation, more may be involved.

The antigenic heterogeneity and instability of Apo AI has made it difficult to produce assay systems for quantifying Apo AI in patient vascular fluid samples. This is because, inter alia, such systems require a reference material (standard) whose immunoreactivity for the system's primary anti-Apo AI antibody is consistent, at the very least, and preferably equivalent to that of the Apo AI in the patient's sample.

Recently, efforts at overcoming problems associated with the antigenic heterogenicity and instability of Apo AI have focused on using monoclonal antibodies (MAB) to identify epitopes on native Apo AI whose expression is consistent or "conserved" under specific isolation and storage conditions. Such epitopes are referred to herein as "conserved native epitopes".

An exemplary conserved native Apo AI epitope, designated epitope A, has been defined by Milthorpe et al., *Arterio.*, 6:285–296 (1986) as being that portion of Apo AI CNBr1 that immunoreacts with MAB 4H1. This was in contrast to epitopes designated C, C' and C", all located in the CNBr2 region of Apo AI, and all of which were found to be "nonconserved" epitopes.

Monoclonal antibodies AI-4, and AI-11, and AI-18 have been identified as anti-Apo AI pan antibodies; that is, antibodies that bind all or most species of Apo AI-containing lipoprotein particles in plasma. See Hogle et al., *J. Lipid. Res.*, 29:1221–1229 (1988); and Curtiss et al., in "Biotechnology of Dyslipoproteinemias: Clinical Applications in Diagnosis and Control", Lenfant et al., eds, pp. 217–226, Raven Press (New York), 1989. However, the specific epitopes on Apo AI with which antibodies AI-4 and AI-11 immunoreact have not been identified.

Apo AI has also been shown to modulate lecithin:cholesterol acyltransferase (LCAT)-mediated cholesterol esterification. Studies by Pownall et al., *Biochem. Biophys. Acta*, 793:149–156 (1984) have shown that an interaction between Apo AI and HDL is required for LCAT activation that results in cholesterol esterification. Moreover, specific regions of Apo AI have been identified that activate LCAT. Polypeptide fragments corresponding to these regions have been synthesized and tested for LCAT activating potential. According to Sparrow et al., *Ann. N.Y. Acad. Sci.*, 384:187–208 (1980), Apo AI fragment residues 148–185 were involved in both activation of LCAT and lipid binding. Similar studies by Fukushima et al., *J Biol. Chem.* 255:10651–10657 (1980) have shown that a synthetic polypeptide corresponding to Apo AI residues 121–164 was 30% as effective as native Apo AI in the activation of cholesterol esterification.

More recent studies with synthetic model polypeptides which mimic the physical properties of native Apo AI have shown that LCAT activation results if the polypeptide associates with HDL. Ponsin et al., *Biochem*, 23:5337–5342 (1984).

BRIEF SUMMARY OF THE INVENTION

Three epitopes on Apo AI have now been discovered that define polypeptides useful to modulate LCAT-mediated cholesterol esterification. In addition, the epitopes represent conserved native epitopes that define polypeptides useful in diagnostic methods to detect Apo AI in vascular fluid samples.

Antibodies immunoreactive with the polypeptide-defined epitopes are also disclosed that are useful in diagonstic and therapeutic methods described herein.

The invention contemplates a diagnostic system, in kit form, comprising, in an amount sufficient to perform at least one assay, an anti-Apo AI antibody molecule that immunoreacts with an Apo AI polypeptide of the invention as disclosed herein.

Thus, in one embodiment, the present invention contemplates a diagnostic system, in kit form, comprising, in an amount sufficient to perform at least one assay, an antibody containing anti-Apo AI antibody molecules that immunoreact with:

(a) Apo AI/HDL,
(b) isolated Apo AI,
(c) Apo AI CNBr2, and
(d) the polypeptide KVQPYLDDFQKKWQEE, (SEQ ID NO 1:12–27), but do not immunoreact with:
(e) Apo AI CNBr1,
(f) Apo AI CNBr3, and
(g) the polypeptide SKDLEEVKAKVQPYLDDE-QKKWQEE (SEQ ID NO 4:1–25),
(h) the polypeptide SKDLEEVKAKVQPYLDDFQ (SEQ ID NO 1:3–21), and
(i) the polypeptide PYLDDFQKKWQEEME-LYRQKVEP (SEQ ID NO 1:15–37).

Preferably, the antibody molecules are operatively linked to an indicating means. The antibody molecules are preferably monoclonal antibody molecules, and more preferably are antibody molecules produced by the hybridoma having ATCC designation HB9201.

In a related embodiment, the invention contemplates a diagnostic system, in kit form, comprising, in an amount sufficient to perform at least one assay, an antibody containing anti-Apo AI antibody molecules that immunoreact with:

(a) Apo AI/HDL,
(b) isolated Apo AI,
(c) Apo AI CNBr2–CNBr3, and
(d) the polypeptide PYLDDFQKKWQEEMEL (SEQ ID NO 1:15–30), but do not immunoreact with:
(e) Apo AI CNBr1,
(f) the polypeptide SKDLEEVKAKVQPYLD-DFQKKWQEE (SEQ ID NO 1:3–27).
(g) the polypeptide LEEVKAKVQPYLDDFQKKWQEE (SEQ ID NO 1:6–27), and
(h) the polypeptide YRQKVEPLRAEL (SEQ ID NO 1:31–42).

Preferably, the antibody molecules are operatively linked to an indicating means. The antibody molecules are preferably monoclonal antibody molecules, and more preferably are antibody molecules produced by the hybridoma having ATCC designation HB8744.

In a related embodiment, a diagnostic system of this invention further comprises an Apo AI polypeptide of the present invention immunoreactive with the antibody in the diagnostic system.

Still further contemplated is a method of assaying the amount of Apo AI in a vascular fluid sample comprising the steps of:

(a) forming an immunoreaction admixture by admixing a vascular fluid sample with:
  (i) an anti-Apo AI antibody of the present invention; and
  (ii) an Apo AI polypeptide with which the antibody immunoreacts, said polypeptide being operatively linked to a solid matrix such that the immunoreaction admixture has both a liquid phase and a solid phase;
(b) maintaining said immunoreaction admixture for a time period sufficient to form an Apo AI-containing immunoreaction product in the solid phase, and
(c) determining the amount of product formed in step (b).

A therapeutic method for increasing the amount of esterified cholesterol in a patient is also contemplated that comprises administering to a patient an esterified cholesterol-increasing amount of an Apo AI polypeptide of this invention.

BRIEF DESCRIPTION OF THE DRAWINGS

In the drawings forming a portion of this disclosure.

The conserved native epitope on Apo AI that is defined by the MAB AI-4 spans CNBr fragments 2 and 3 and is comprised of amino acid residues sequence 99-114. The conserved native epitope on Apo AI that is defined by the MAB AI-11 is confined to CNBr2 from the amino acid residue sequence 96-111. The conserved native epitope on Apo AI that is defined by the MAB AI-18 is confined to CNBR2 from the amino acid residue sequence 95–105.

Figure 2:
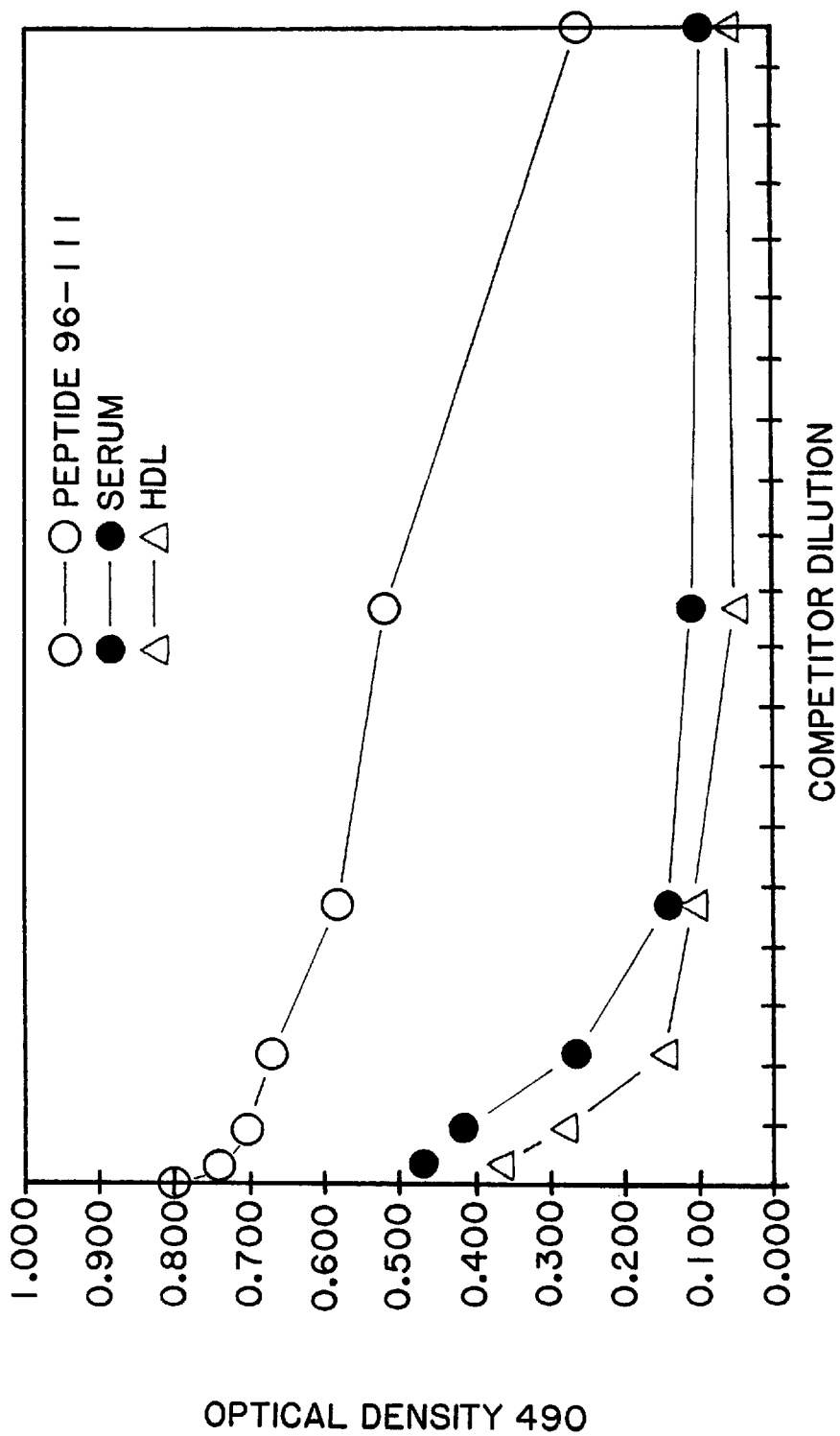

FIG. 2 illustrates the ability of Apo AI/HDL, HDL present in fresh plasma, and the polypeptide AI96-111 to competitively inhibit MAE AI-11 from immunoreacting with AI96-111. Protein concentrations were determined according to the method of Markwell et al., *Anal. Biochem.*, 87:206–220 (1978). The units on the X-axis vary linearly with respect to the three competitors used in the assay. The data points for Apo AI/HDL correspond to a starting concentration of 1 mg/ml followed by 5 serial 2-fold dilutions. The data points for HDL present in fresh plasma correspond to a starting dilution of 1:10 followed by 6 serial 2-fold dilutions.

Polypeptide AI 96-111 is diluted as above for plasma with a starting concentration of 1 mg/ml.

Figure 3:
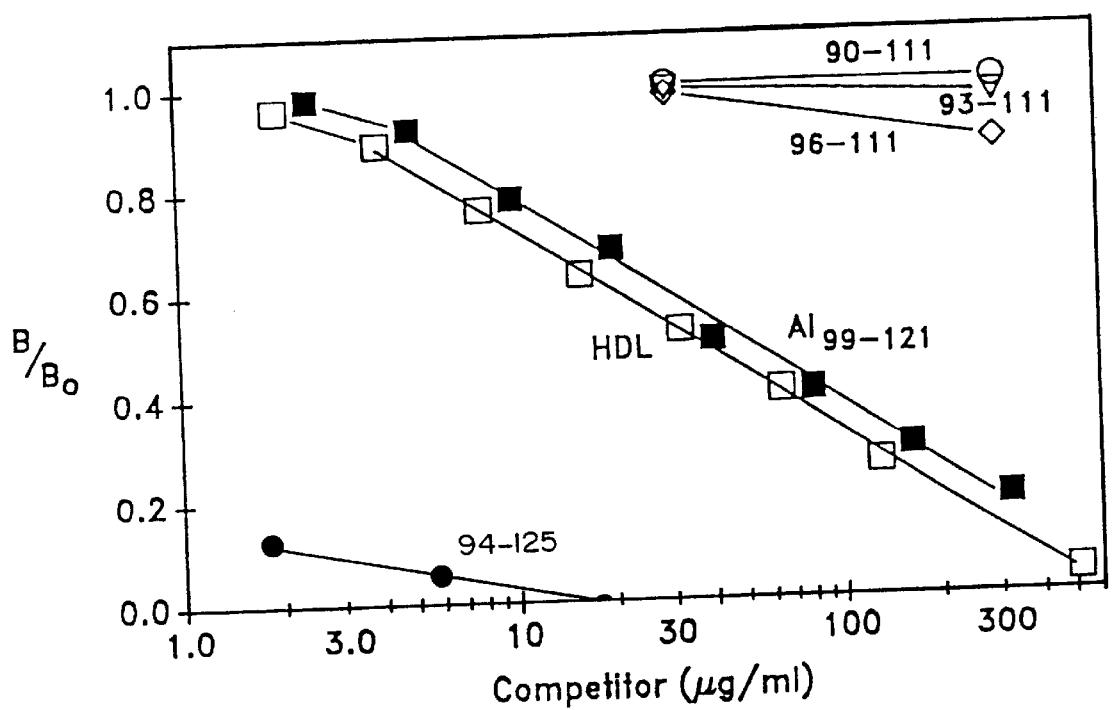

FIG. 3 illustrates the ability of Apo AI/HDL and the polypeptides AI94-125 and AI99-121 to competitively inhibit MAB AI-4 from immunoreacting with Apo AI/HDL. Polypeptides AI90-111, AI93-111 and AI96-111 are not competitive inhibitors. The concentration of the competitor is shown in μg protein/ml determined as described in FIG. 2.

Figure 1:
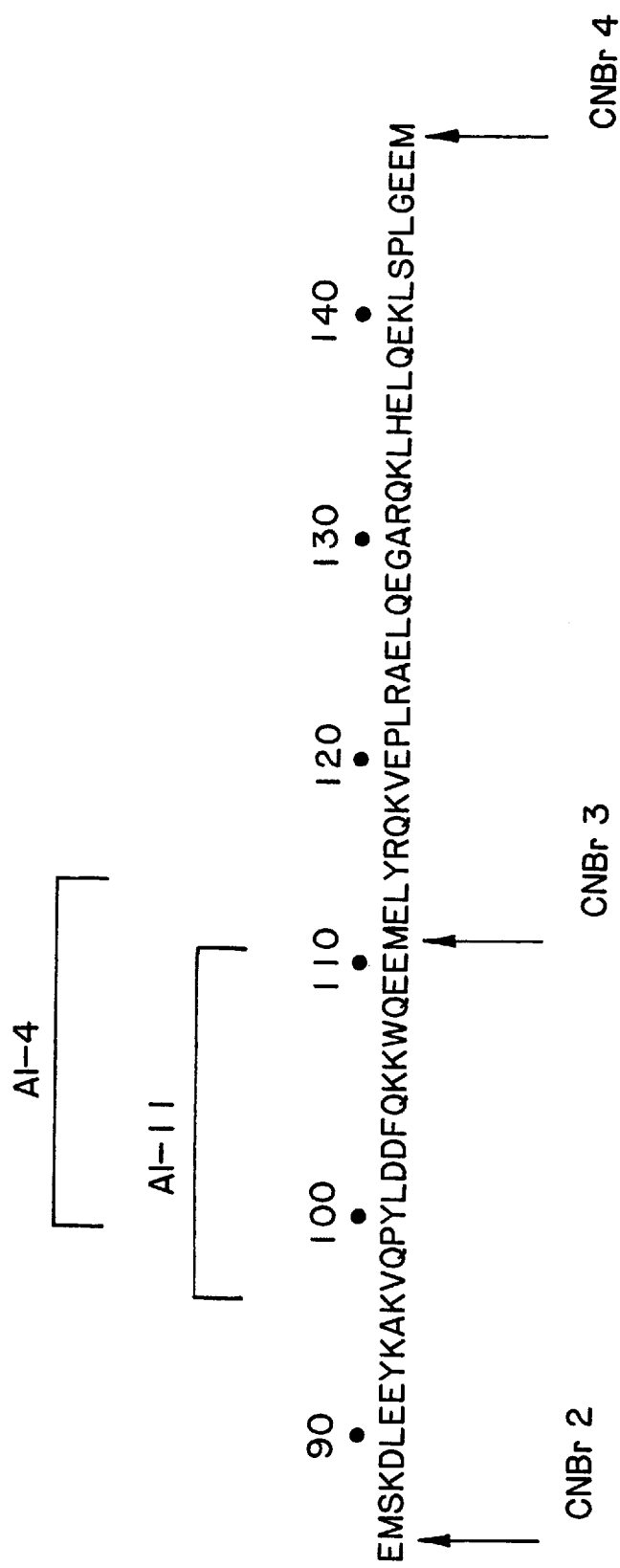
FIG. 1 illustrates the amino acid residue sequence of Apo AI (SEQ ID NO 1), as reported by Brewer et al., *Biochem. Biophys. Res. Comm.*, 80:623–630 (1978), from amino acid residue positions 85 through 148 using the single letter code. Apo AI CNBr2, which is formed by cleavage at the methionine (M) residues located at positions 86 and 112, corresponds in sequence to positions 87 through 111 with the carboxy terminal methionine being converted to homoserine lactone. Apo AI CNBr3, which is formed by cleavage at the methionine (M) residues located at positions 112 and 148, corresponds in sequence to positions 113 through 147 with the carboxy terminal methionine being converted to homoserine lactone.
Figure 4:
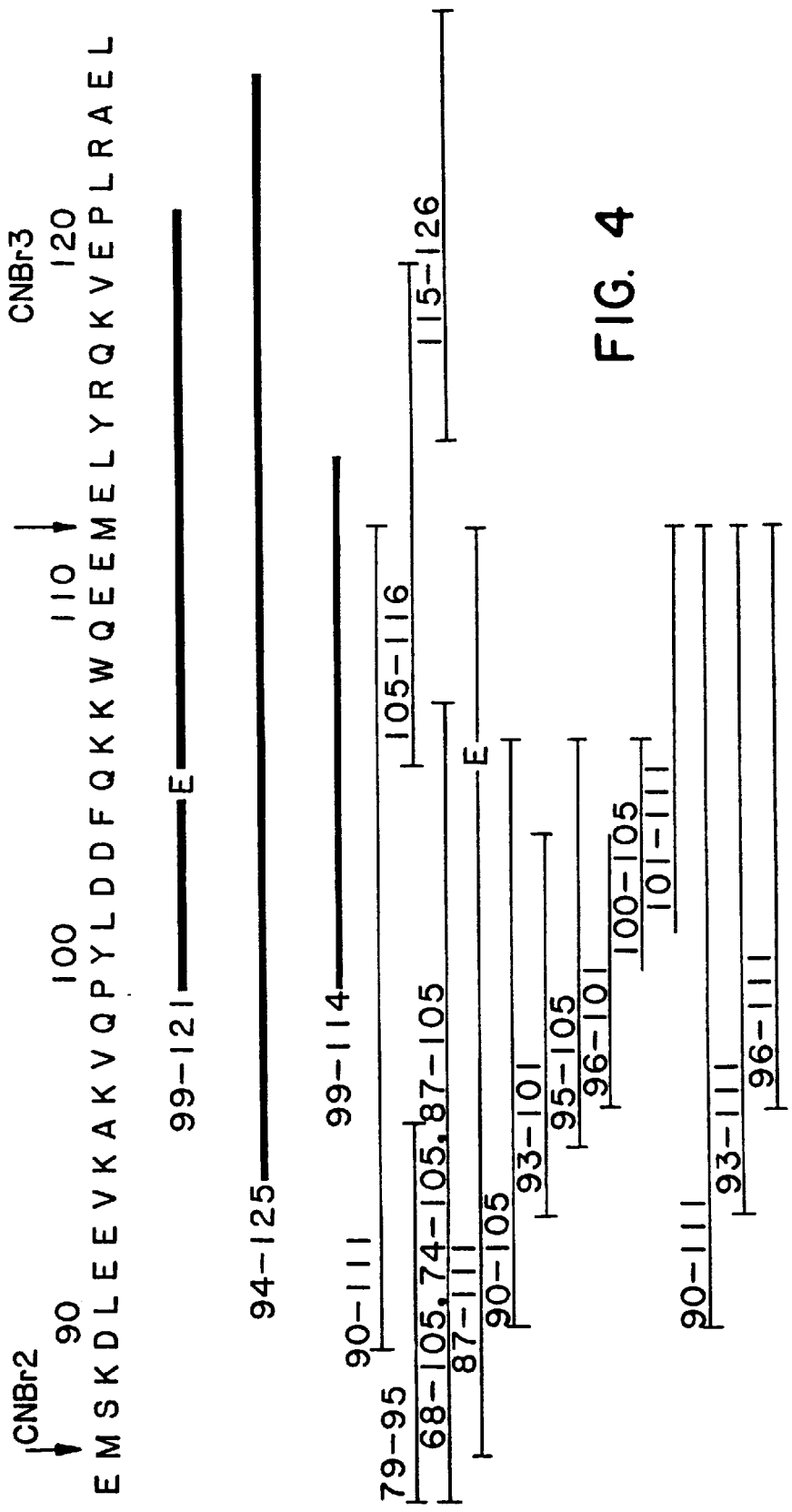

FIG. 4 illustrates the amino acid residue sequence of a portion of Apo AI as described in FIG. 1 (SEQ ID NO 1:1–42). A conserved native epitope is defined by MAB AI-4 and the epitope is immunologically mimicked by the polypeptide AI99-121, which is shown as a bold line. Polypeptides AI94-125 and AI99-121, also in bold, also immunoreacts with MAB AI-4 and mimics the epitope. Polypeptides derived from Apo AI which do not immunoreact with MAB AI-4 nor mimic the epitope are shown as thin lines. Alignments of the thin lines with actual Apo AI sequences are approximate with respect to the amino acid residue sequence of Apo AI, and the actual span of amino acid residues which comprise the thin line polypeptides are designated numerically.

Figure 5:
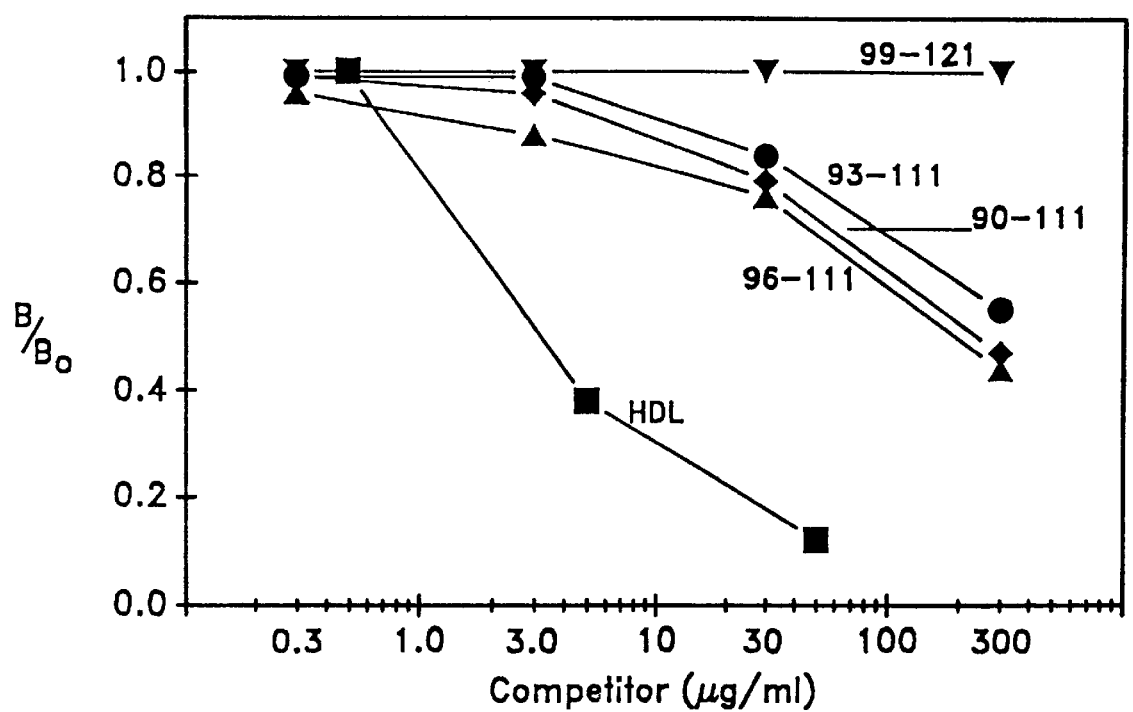

FIG. 5 illustrates the ability of Apo AI/HDL and the polypeptides AI90-111, AI93-111, and AI96-111 to competitively inhibit MAB AI-11 from immunoreacting with Apo AI/HDL. Polypeptide AI99-121 is not a competitive inhibitor.

Figure 6:
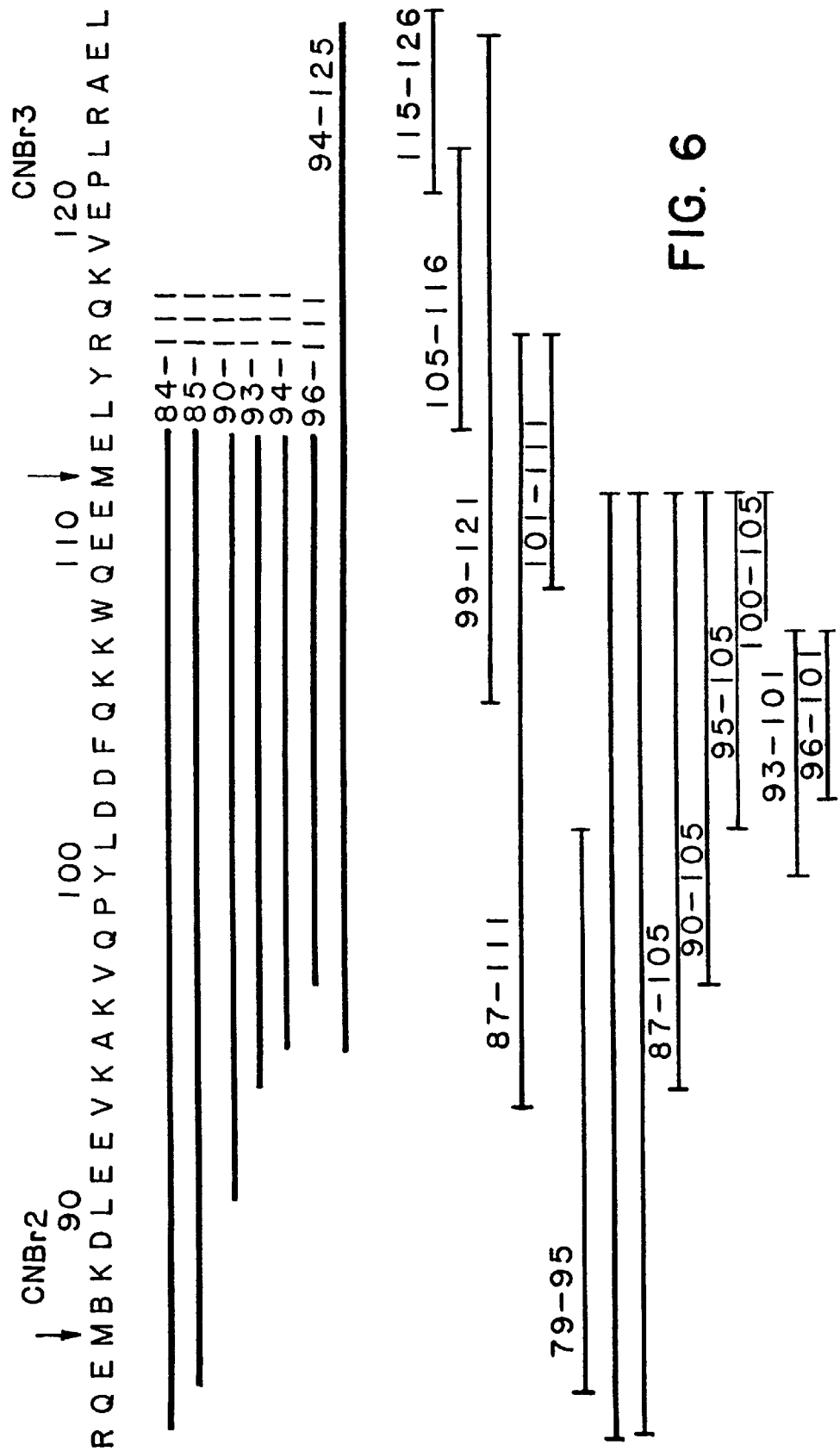

FIG. 6 illustrates the amino acid residue sequence of a portion of Apo AI as described in FIG. 1 (SEQ ID NO 2). A conserved native epitope is defined by MAB AI-11, and the epitope is immunologically mimicked by polypeptide AI96-111, which is shown as a bold line. Polypeptides AI84-111, AI85-111, AI90-111, AI93-111, AI94-111 and AI94-125, also in bold, also immunoreact with MAB AI-11 and mimic the epitope. Polypeptides derived from Apo AI which do not immunoreact with MAB AI-11 nor mimic the epitope are shown as thin lines. Alignments of the polypeptides which do not react with MAE AI-11 are as described in FIG. 4.

Figure 7:
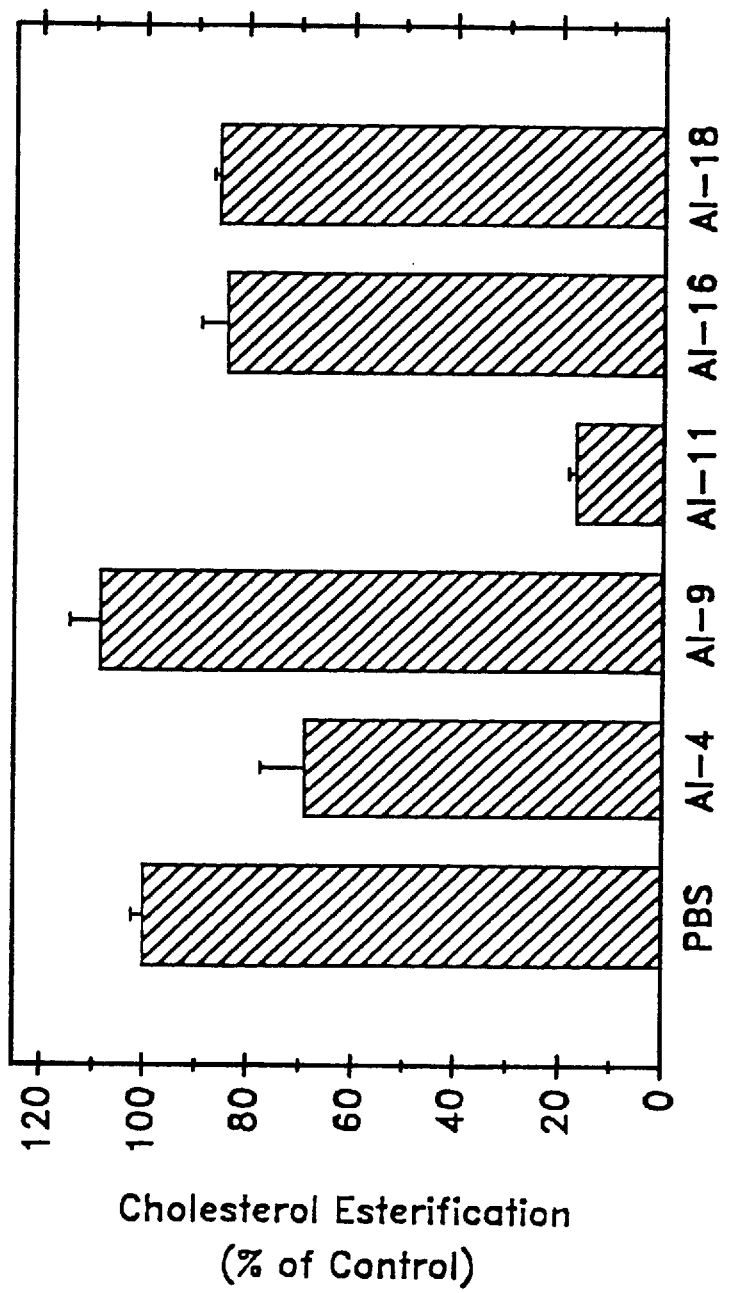

FIG. 7 illustrates the ability of the anti-Apo AI monoclonal antibodies of this invention to inhibit LCAT-mediated cholesterol esterification as described in Example 11.

Figure 8:
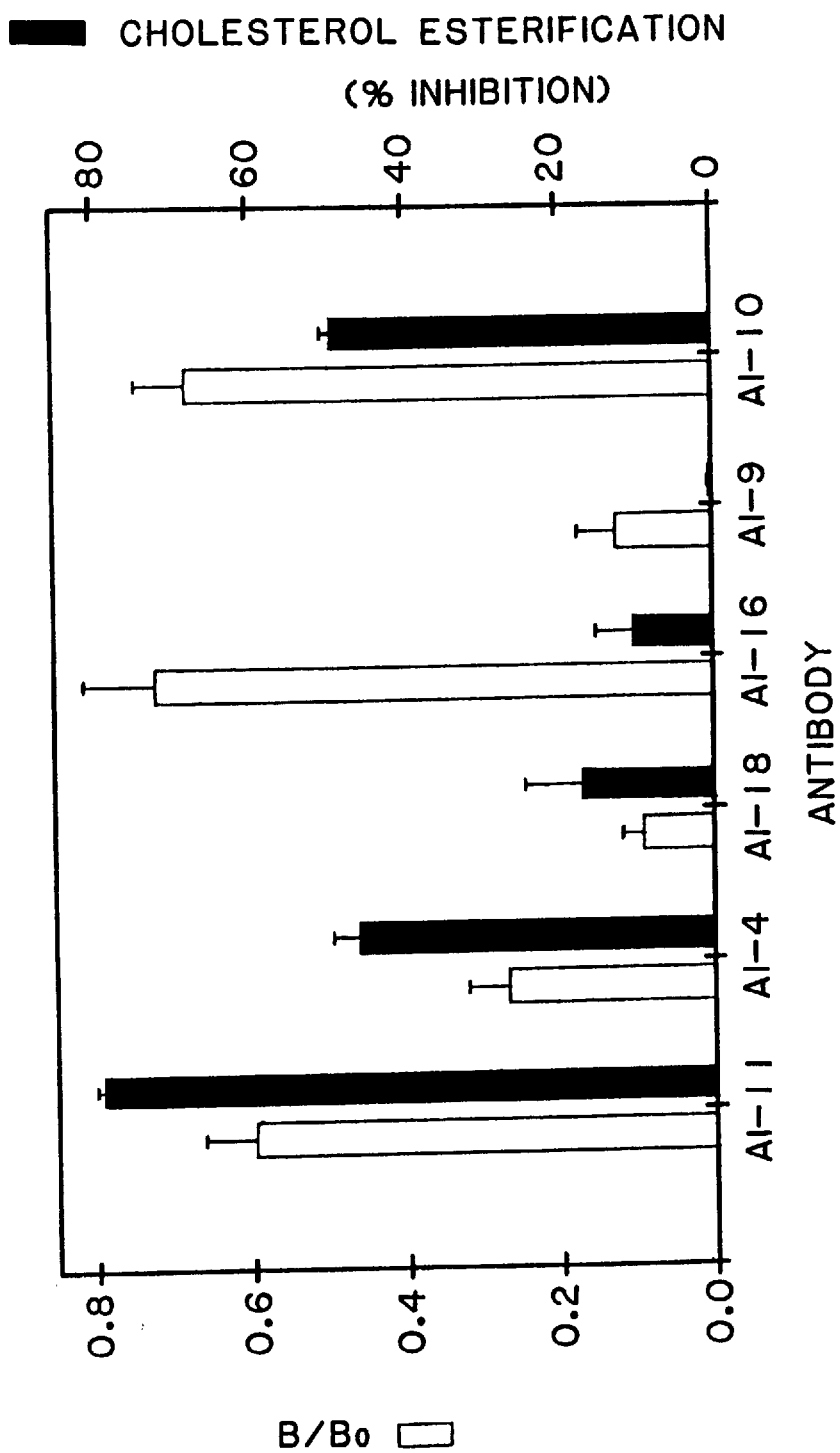

FIG. 8 provides a comparison of an antibody's ability to bind to proteoliposomes with its ability to inhibit LCAT-mediated cholesterol esterification as described in Example 11. Binding data (open bars) was taken from a fluid-phase immunoassay where the conditions of the LCAT assay were duplicated. Apo A-I was used at a concentration of 220 ug/ml and antibodies were added at a 4-fold molar excess. LPDP and B-mercaptoethanol were added as in the LCAT assay. Bars represent means ± S.E. for two experiments performed in duplicate. Data for inhibition of LCAT-mediated esterification (hatched bars) was taken from FIG. 7 and is expressed here as the % of inhibition.

DETAILED DESCRIPTION OF THE INVENTION

A. Definitions

Amino Acid Residue: The amino acid residues described herein are preferred to be in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.,* 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates either a peptide bond to a further sequence of one or more amino acid residues or a covalent bond to a carboxyl or hydroxyl end group.

Apo AI/HDL: Designates Apo AI when it is present on HDL particles.

Delipidated Apo AI: Refers to Apo AI that is substantially free of associated lipids.

Homoserine Lactone: Refers to a derivatized carboxy terminal methionine residue on a polypeptide that is formed by conventional cyanogen bromide (CNBr) cleavage of proteins. Homoserine lactone is not normally found in proteins, and is preferably not present in a polypeptide of this invention.

Isolated Apo AI: Designates Apo AI that is substantially free of both associated lipids and other proteins, such as those, like Apo AII, that are typically found on HDL in addition to Apo AI.

Polypeptide and Peptide: Polypeptide and peptide are terms used interchangeably herein to designate a linear series of amino acid residues connected one to the other by peptide bonds between the alpha-amino and carboxy groups of adjacent residues.

Protein: Protein is a term used herein to designate a linear series of greater than about 50 amino acid residues connected one to the other as in a polypeptide.

Synthetic peptide: refers to a chemically produced chain of amino acid residues linked together by peptide bonds that is free of naturally occurring proteins and fragments thereof.

B. Polypeptides

As used herein, the phrase "Apo AI polypeptide" refers to a polypeptide whose amino acid residue sequence corresponds, and preferably is identical to a portion of the Apo AI molecule.

In one embodiment, an Apo AI polypeptide of the present invention comprises no more than about 60 amino acid residues, preferably no more than about 32 amino acid residues, and includes an amino acid residue sequence represented by the formula (SEQ ID NO 1:12–27):-KVQPYLDDFQKKWQEE-. This polypeptide defines a conserved native epitope on Apo AI that is defined by the ability of the polypeptide to immunoreact with the monoclonal antibody MAB AI-11 (i.e., the polypeptide defines a MAE AI-11 epitope). In preferred embodiments, the polypeptide has an amino acid residue sequence represented by a formula selected from the group consisting of:
QEMSKDLEEVKAKVQPYLDDFQKKWQEE,
EMSKDLEEVKAKVQPYLDDFQKKWQEE,
LEEVKAKVQPYLDDFQKKWQEE,
VKAKVQPYLDDFQKKWQEE,
KAKVQPYLDDFQKKWQEE,
KAKVQPYLDDFQKKWQEEMELYRQKVEPLRAE, and
KVQPYLDDFQKKWQEE, respectively, SEQ ID NOs 2:2–29, 1:1–27, 1:6–27, 1:9–27, 1:10–27, 1:10–41, and 1:12–27.

A related APO AI polypeptide defining a MAB AI-11 epitope comprises 26 to 60 amino acid residues, preferably 27 to 32 amino acid residues, and includes an amino acid residue sequence represented by the formula (SEQ ID NO 1:12–27):-KVQPYLDDFQKKWQEE-. Preferably the polypeptide has an amino acid residue sequence represented by a formula selected from the group consisting of:
QEMSKDLEEVKAKVQPYLDDFQKKWQEE,
EMSKDLEEVKAKVQPYLDDFQKKWQEE, and
KAKVQPYLDDFQKKWQEEMELYRQKVEPLRAE,
respectively, SEQ ID NOs 2:2–29, 1:1–27 and 1:10–41.

Another related Apo AI polypeptide defining a MAB AI-11 epitope comprises no more than 25 amino acid residues, preferably no more than about 22 amino acid residues, and includes an amino acid residue sequence represented by the formula (SEQ ID NO 1:12–27):-KVQPYLDDFQKKWQEE-. In preferred embodiments, the polypeptide has an amino acid residue sequence represented by a formula selected from the group consisting of:
LEEVKAKVQPYLDDFQKKWQEE,
VKAKVQPYLDDFQKKWQEE,
KAKVQPYLDDFQKKWQEE, AND
KVQPYLDDFQKKWQEE, respectively, SEQ ID NOs 1:6–27, 1:9–27, 1:10–27 and 1:12–27.

In another embodiment, an Apo AI polypeptide of this invention comprises no more than about 60 amino acid residues and includes an amino acid residue sequence represented by the formula (SEQ ID NO 3:6–21):-PYLDDXQKKWQEEMEL-, wherein X is either E or F. This polypeptide defines a conserved native epitope on Apo AI that is defined by the ability of the polypeptide to immunoreact with the monoclonal antibody MAE AI-4 (i.e., the polypeptide defines a MAB AI-4 epitope). Preferably, the Apo AI polypeptide includes an amino acid residue sequence represented by the formula (SEQ ID NO 3:6–28):-PYLDDXQKKWQEEMELYRQKVEP-, wherein X is either E or F. In preferred embodiments, the polypeptide has an amino acid residue represented by a formula selected from the group consisting of:
KAKVQPYLDDXQKKWQEEMEL,
KAKVQPYLDDXQKKWQEEMELYRQKVEPLRAE,
QPYLDDXQKKWQEEMEL,
QPYLDDXQKKWQEEMELYRQKVEP,
PYLDDXQKKWQEEMEL, and
PYLDDXQKKWQEEMELYRQKVEP,
respectively, SEQ ID NOs 3:1–21, 3:1–32, 3:5–21, 3:5–28, 3:6–21 and 3:6–28.

In another embodiment, an Apo AI polypeptide of this invention comprises no more than about 40 amino acid residues and includes an amino acid residue sequence represented by the formula (SEQ ID NO 1:11–21):-AKVQPYLDDFQ-. This polypeptide defines a conserved native epitope on Apo AI that is defined by the ability of the polypeptide to immunoreact with the monoclonal antibody MAB AI-18 (i.e., the polypeptide defines a MAE AI-18 epitope). In preferred embodiments, the polypeptide has an amino acid residue sequence represented a formula selected from the group consisting of:
LEEVKAKVQPYLDDFQ,
LEEVKAKVQPYLDDFQKKWQEE,
SKDLEEVKAKVQPYLDDFQ, and
AKVQPYLDDFQ, respectively, SEQ ID NOs 1:6–21, 1:6–27, 1:3–21 and 1:11–21.

It is preferred that an Apo AI polypeptide of this invention is free of homoserine lactone.

Preferred Apo AI polypeptides, their designations, and their Apo AI amino acid residue positions are shown in Table 1.

TABLE 1

| Polypeptide Designation | SEQ ID NO | Amino Acid Residue Sequence |
|---|---|---|
| AI84-111 | 2:2–29 | QEMSKDLEEVKAKVQPYLDDFQKKWQEE |
| AI85-111 | 1:1–27 | EMSKDLEEVKAKVQPYLDDFQKKWQEE |
| AI87-111 | 1:3–27 | SKDLEEVKAKVQPYLDDFQKKWQEE |
| AI90-111 | 1:6–27 | LEEVKAKVQPYLDDFQKKWQEE |
| AI93-111 | 1:9–27 | VKAKVQPYLDDFQKKWQEE |
| AI94-111 | 1:10–27 | KAKVQPYLDDFQKKWQEE |
| AI94-114[1] | 1:10–30 | KAKVQPYLDDXQKKWQEEMEL |
| AI94-125[1] | 1:10–43 | KAKVQPYLDDXQKKWQEEMELYRQKVEPLRAE |
| AI96-111 | 1:12–27 | KVQPYLDDFQKKWQEE |
| AI98-114[1] | 3:5–21 | QPYLDDXQKKWQEEMEL |
| AI98-121[1] | 3:5–28 | QPYLDDXQKKWQEEMELYRQKVEP |
| AI99-114[1] | 3:6–21 | PYLDDXQKKWQEEMEL |
| AI99-121[1] | 3:6–28 | PYLDDXQKKWQEEMELYRQKVEP |
| AI90-105 | 1:6–21 | LEEVKAKVQPYLDDFQ |
| AI87-105 | 1:3–21 | SKDLEEVKAKVQPYLDDFQ |
| AI95-105 | 1:11–21 | AKVQPYLDDFQ |

[1]An "X" at amino acid residue position 104 indicates that either an E for glutamic acid or an F for phenylalanine is present at residue position 104.

Preferably, an Apo AI polypeptide of this invention is further characterized by its ability to immunologically mimic an epitope (antigenic determinant) expressed by Apo AI on substantially all HDL.

As used herein, the phrase "immunologically mimic" in its various grammatical forms refers to the ability of an Apo AI polypeptide of this invention to immunoreact with an antibody of the present invention that recognizes a conserved native epitope of Apo AI as defined herein.

It should be understood that a subject polypeptide need not be identical to the amino acid residue sequence of Apo AI, so long as it includes the required sequence and is able to immunoreact with antibodies of the present invention.

A subject polypeptide includes any analog, fragment or chemical derivative of a polypeptide whose amino acid residue sequence is shown herein so long as the polypeptide is capable of immunologically mimicking an Apo AI native conserved epitope. Therefore, a present polypeptide can be subject to various changes, substitutions, insertions, and deletions where such changes provide for certain advantages in its use.

The term "analog" includes any polypeptide having an amino acid residue sequence substantially identical to a sequence specifically shown herein in which one or more residues have been conservatively substituted with a functionally similar residue and which displays the ability to mimic Apo AI as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

A polypeptide is free of homoserine lactone when there is no detectable homoserine lactone present in the polypeptide when subjected to conventional amino acid analysis able to indicate the presence of homoserine lactone or other amino acids. Amino acid analysis methods suitable to detect homoserine lactone are generally well known in the art.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a Apo AI because one or more conservative or non-conservative substitutions have been made, usually no more than about 30 number percent, more usually no more than 20 number percent, and preferably no more than 10 number percent of the amino acid residues are substituted, except that the proline residue at position 99 cannot be substituted or deleted where additional residues have been added at either terminus for the purpose of providing a "linker" by which the polypeptides of this invention can be conveniently affixed to a label or solid matrix, or carrier, the linker residues do not form Apo AI epitopes, i.e., are not similar is structure to the Apo AI. Labels, solid matrices and carriers that can be used with the polypeptides of this invention are described hereinbelow.

Amino acid residue linkers are usually at least one residue and can be 40 or more residues, more often 1 to 10 residues, but do not form Apo AI epitopes. Typical amino acid residues used for linking are tyrosine, cysteine, lysine, glutamic and aspartic acid, or the like. In addition, a subject polypeptide can differ, unless otherwise specified, from the natural sequence of Apo AI by the sequence being modified by terminal-$NH_2$ acylation, e.g., acetylation, or thioglycolic acid amidation, by terminal-carboxlyamidation, e.g., with ammonia, methylamine, and the like.

When coupled to a carrier to form what is known in the art as a carrier-hapten conjugate, an Apo AI polypeptide of the present invention is capable of inducing antibodies that immunoreact with Apo AI, preferably Apo AI when it is part of an HDL particle (Apo AI/HDL). In view of the well established principle of immunologic cross-reactivity, the present invention therefore contemplates antigenically related variants of the polypeptides shown in Table 1. An "antigenically related variant" is a subject polypeptide that is capable of inducing antibody molecules that immunoreact with a polypeptide from Table 1 and Apo AI.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

An Apo AI polypeptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

An Apo AI polypeptide can be used, inter alia, in the diagnostic methods and systems of the present invention to detect Apo AI present in a body sample, or can be used to prepare an inoculum as described herein for the preparation of antibodies that immunoreact with conserved epitopes on Apo AI.

In addition, an Apo AI polypeptide of this invention can be used in the therapeutic methods of the present invention to increase esterification of cholesterol in a patient.

C. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site", is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

An antibody of the present invention, i.e., an anti-Apo AI antibody, in one embodiment is characterized as being capable of immunoreacting with 1) Apo AI present on HDL particles (Apo AI/HDL), 2) isolated Apo AI, 3) Apo AI (CNBr2–CNBr3), and 4) the polypeptide PYLD-DFQKKWQEEMEL (SEQ ID NO 1:15–30), and being substantially free of antibody molecules that immunoreact with 1) Apo AI CNBr1, and 2) the polypeptides:
SKDLEEVKAKVQPYLDDFQKKWQEE,
LEEVKAKVQPYLDDFQKKWQEE, and
YRQKVEPLRAEL,
respectively SEQ ID NOs 1:3–27, 1:6–27 and 1:31–42.

In another embodiment, an anti-Apo AI antibody is characterized as being capable of immunoreacting with 1) Apo AI/HDL, 2) isolated Apo AI, 3) Apo AI CNBr2, and 4) the polypeptide KVQPYLDDFQKKWQEE (SEQ ID NO 1:12–27), and being substantially free of antibody molecules that immunoreact with 1) Apo AI CNBr1, 2) Apo AI CNBr3, and 3) the polypeptides:
SKDLEEVKAKVQPYLDDEQKKWQEE,
SKDLEEVKAKVQPYLDDFQ, and
PYLDDFQKKWQEEMELYRQKVEP,
respectively, SEQ ID NOs 4:1–25, 1:3–21 and 1:15–37.

Antibody immunoreactivity with Apo AI-containing antigens can be measured by a variety of immunological assays known in the art. Exemplary immunoreaction of an anti-Apo AI antibody with a CNBr fragment is described in Example 8. Direct binding with Apo AI/HDL, isolated Apo AI (prepared as described in Example 4), and with Apo AI polypeptides can be assayed at least by the methods described in Example 9.

An antibody of the present invention is typically produced by immunizing a mammal with an inoculum containing an Apo AI polypeptide of this invention and thereby induce in the mammal antibody molecules having immunospecificity for Apo AI polypeptide. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The antibody so produced can be used, inter alia, in the diagnostic methods and systems of the present invention to detect Apo AI present in a body sample. See, for example, the method described in Example 9.

The word "inoculum" in its various grammatical forms is used herein to describe a composition containing an Apo AI polypeptide of this invention as an active ingredient used for the preparation of antibodies against an Apo AI polypeptide.

When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as glutaraldehyde, Klipstein, et al., J. Infect. Dis., 147:318–326 (1983) and the like, or the use of carbodiimide technology as in the use of a water-soluble carbodiimide to form amide links to the carrier. For a review of protein conjugation or coupling through activated functional groups, see Aurameas, et al., Scand. J. Immunol., 1:7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine:D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The techniques of polypeptide conjugation or coupling through activated functional groups presently known in the art are particularly applicable. See, for example, Aurameas, et al., Scand. J. Immunol., Vol. 8, Suppl. 7:7–23 (1978) and U.S. Pat. Nos. 4,493,795, 3,791,932 and No. 3,839,153. In addition, a site directed coupling reaction can be carried out so that any loss of activity due to polypeptide orientation after coupling can be minimized. See, for example, Rodwell et al., Biotech., 3:889–894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

A preferred anti-Apo AI antibody is a monoclonal antibody and is used herein as exemplary of an anti-Apo AI antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody, in one embodiment, is characterized as being capable of immunoreacting with 1) Apo AI/HDL, 2) isolated Apo AI, 3) Apo AI CNBr2–CNBr3, and 4) the polypeptide PYLDDFQKKWQEEMEL (SEQ ID NO 1:15–30), and being substantially free of antibody molecules that immunoreact with 1) Apo AI CNBr1, and 2) the polypeptides:
SKDLEEVKAKVQPYLDDFQKKWQEE,
LEEVKAKVQPYLDDFQKKWQEE, and
YRQKVEPLRAEL, respectively
SEQ ID NOs 1:3–27, 1:6–27 and 1:31–42. Particularly preferred is the monoclonal antibody produced by the hybridoma AI-4, having an ATCC accession number HB8744.

In another embodiment, a monoclonal antibody is characterized as being capable of immunoreacting with 1) Apo AI/HDL, 2) isolated Apo AI, 3) Apo AI CNBr2, and 4) the polypeptide KVQPYLDDFQKKWQEE (SEQ ID NO 1:12–27), and being substantially free of antibody molecules that immunoreact with 1) Apo AI CNBr1, 2) Apo AI CNBr3, and 3) the polypeptides:
SKDLEEVKAKVQPYLDDEQKKWQEE,
SKDLEEVKAKVQPYLDDFQ, and
PYLDDFQKKWQEEMELYRQKVEP,
respectively SEQ ID NOs 4:1–25, 1:3–21 and 1:15–37. Particularly preferred in this embodiment is the monoclonal antibody produced by the hybridoma AI-11, having an ATCC accession number HB9201.

A monoclonal antibody is typically composed of antibodies produced by clones of a single cell called a hybridoma that secretes (produces) but one kind of antibody molecule.

The hybridoma cell is formed by fusing an antibody-producing cell and a myeloma or other self-perpetuating cell line. The preparation of such antibodies was first described by Kohler and Milstein, *Nature* 256:495–497 (1975), which description is incorporated by reference. The hybridoma supernates so prepared can be screened for the presence of antibody molecules that immunoreact with an Apo AI polypeptide, or for inhibition of binding to HDL by the Apo AI polypeptides of this invention.

Briefly, to form the hybridoma from which the monoclonal antibody composition is produced, a myeloma or other self-perpetuating cell line is fused with lymphocytes obtained from the spleen of a mammal hyperimmunized with an Apo AI antigen, such as is present in an Apo AI-containing lipoprotein particles, or with an Apo AI polypeptide of this invention. The polypeptide-induced hybridoma technology is described by Niman et al., *Proc. Natl. Sci. U.S.A.*, 80:4949–4953 (1983), which description is incorporated herein by reference.

It is preferred that the myeloma cell line used to prepare a hybridoma be from the same species as the lymphocytes. Typically, a mouse of the strain 129 GlX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the radioimmunoassay (RIA) and the enzyme linked immunosorbent assay (ELISA) described in Examples 10 and 9, respectively.

A monoclonal antibody of the present invention can also be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/1 glucose, 20 mm glutamine, and 20% fetal calf serum. An exemplary inbred mouse strain is the Balb/c.

The monoclonal antibodies of this invention can be used in the same manner as disclosed herein for antibodies of the present invention.

For example, the monoclonal antibody can be used in the diagnostic methods and systems disclosed herein where formation of an Apo AI-containing immunoreaction product is desired.

A hybridoma useful in producing a subject monoclonal antibody, i.e., MAB AI-4 and MAB AI-11 are hybridomas 611AV63C2.111 and H10308.1011, said hybridomas being deposited pursuant to Budapest Treaty Requirements with the American Type Culture Collection (ATCC), Rockville, Md. 20852 U.S.A. on Mar. 5, 1985 and Sep. 16, 1986, respectively, and given the ATCC designations HB8744 and HB9201, respectively. It should be noted that hybridoma ATCC 1580 can be used, as is well known in the art, to produce other immortal cell lines that produce a subject monoclonal antibody, and thus production of a subject monoclonal antibody is not dependent on culturing hybridomas by ATCC HB8744 and HB9201 per se.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci.*, 86:5728–5732 (1989); and Huse et al., *Science*, 246:1275–1281 (1981).

Also contemplated by this invention is the hybridoma cell, and cultures containing a hybridoma cell that produce a monoclonal antibody of this invention.

D. Diagnostic Systems

The present invention also describes a diagnostic system, preferably in kit form, for assaying for the presence of Apo AI or an Apo AI polypeptide in a fluid sample. A diagnostic system includes, in an amount sufficient for at least one assay, a subject Apo AI polypeptide and/or a subject antibody or monoclonal antibody, as a separately packaged immunochemical reagent. Instructions for use of the packaged reagent are also typically included.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence of or to quantitate Apo AI in a sample, such as blood, plasma or serum, comprises a package containing at least one Apo AI polypeptide of this invention. In another embodiment, a diagnostic system of the present invention for assaying for the presence or amount of Apo AI or an Apo AI polypeptide in a sample further includes an anti-Apo AI antibody composition of this invention. An exemplary diagnostic system is described in Example 9.

In preferred embodiments, a diagnostic system of the present invention further includes a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$ indium of $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of Apo AI in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in preferred embodiments, an Apo AI polypeptide or a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The term "package" refers to a solid matrix or material such as glass, plastic (e.g., polyethylene, polypropylene and polycarbonate), paper, foil and the like capable of holding within fixed limits a diagnostic reagent such as a polypeptide, antibody or monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

E. Assay Methods

The present invention contemplates various immunoassay methods for determining the amount of Apo AI in a biological fluid sample using a polypeptide, polyclonal antibody or monoclonal antibody of this invention as an immunochemical reagent to form an immunoreaction product whose amount relates, either directly or indirectly, to the amount of Apo AI in the sample. Those skilled in the art will understand that there are numerous well known clinical diagnostic chemistry procedures in which an immunochemical reagent of this invention can be used to form an immunoreaction product whose amount relates to the amount of Apo AI present in a body sample. Thus, while exemplary assay methods are described herein, the invention is not so limited.

Various heterogeneous and homogeneous protocols, either competitive or noncompetitive, can be employed in performing an assay method of this invention. For example, the present invention contemplates a competitive method for assaying the amount of Apo AI in a vascular fluid sample which comprises the steps of:

(a) Forming an immunoreaction admixture by admixing a vascular fluid sample with:
  (i) an antibody of the present invention, preferably a monoclonal antibody, and
  (ii) an Apo AI polypeptide of the present invention that is able to immunoreact with the antibody added in step (i).

Preferably, the vascular fluid sample is provided as a known amount of blood, or a blood derived product such as serum or plasma. Regardless of the type of sample used, it is preferably obtained from a person who has fasted at least about 12 hours as is known in the art. Such a sample is referred to as a "fasting" sample. It is also noted that where serum or plasma is used as the sample, that sample need not be subjected to treatment with a denaturing or chaotropic agent for purposes of altering the expression of the Apo AI epitope being assayed.

In one embodiment, the diagnostic method includes forming an immunoreaction admixture by admixing a vascular fluid sample with:

(i) an anti-Apo AI antibody molecule that immunoreacts with 1) Apo AI/HDL, 2) isolated Apo AI, 3) Apo AI CNBr2–CNBr3, and 4) the polypeptide PYLDDFQKKWQEEMEL (SEQ ID NO 1:15–30), and is substantially free of antibody molecules that immunoreact with 1) Apo AI CNBr1, and 2) the polypeptides:
SKDLEEVKAKVQPYLDDFQKKWQEE,
LEEVKAKVQPYLDDFQKKWQEE, and
YRQKVEPLRAEL, respectively
SEQ ID NOs 1:3–27, 1:6–27 and 1:31–42; and (ii) an Apo AI polypeptide of the present invention that includes an amino acid residue sequence represented by the formula (SEQ ID NO 3:6– 21):-PYLDDXQKKWQEEMEL-, and preferably includes an amino acid residue sequence represented by the formula (SEQ ID NO 3:6–28):-PYLDDXQKKWQEEMELYRQKVEP-. In particular preferred embodiments, the antibody is the monoclonal antibody produced by the hybridoma cell line having the ATCC designation HB 8744, and the polypeptide is selected from the group polypeptides shown in Table 1 consisting of AI99-121, AI94-125, AI94-114, AI98-114, AI98-121, and AI99-114.

In another embodiment, the immunoreaction admixture is formed by admixing a vascular fluid sample with:
(i) an anti-Apo AI antibody molecule that immunoreacts with 1) Apo AI/HDL, 2) isolated Apo AI, 3) Apo AI CNBr2, and 4) the polypeptide KVQPYLDDFQKKWQEE (SEQ ID NO 1:12–27), and is substantially free of antibody molecules that immunoreact with 1) Apo AI CNBr1, 2) Apo AI CNBr3, and 3) the polypeptides:
SKDLEEVKAKVQPYLDDEQKKWQEE,
SKDLEEVKAKVQPYLDDFQ, and
PYLDDFQKKWQEEMELYRQKVEP,
respectively SEQ ID NOs 4:1–25, 1:3–21 and 1:15–37; and
(ii) an Apo AI polypeptide of the present invention that includes an amino acid residue sequence represented by the formula (SEQ ID NO 1:12–27):-KVQPYLDDFQKKWQEE-. In particularly preferred embodiments, the antibody is the monoclonal antibody produced by the hybridoma cell line having the ATCC designation HB9201, and the polypeptide is selected from the group of polypeptides shown in Table 1 consisting of AI96-111, AI93-111, AI84-111, AI85-111, AI87-111, AI94-111, AI94-125, and AI90-111.

Preferably, the amount of antibody that is admixed is known. Further preferred are embodiments where the antibody is labeled, i.e., operatively linked to an indicating means such as an enzyme, radionuclide and the like.

Preferably, the Apo AI polypeptide is present as part of a solid support, i.e., operatively linked to a solid matrix, so that the immunoreaction admixture formed has a solid and a liquid phase. Further preferred are embodiments wherein the amount of polypeptide present in the immunoreaction admixture is an amount sufficient to form an excess of epitopes relative to the number of antibody combining sites present in the immunoreaction admixture capable of immunoreacting with those epitopes.

(b) The immunoreaction admixture is maintained under biological assay conditions for a predetermined time period such as about 10 minutes to about 16–20 hours at a temperature of about 4 degrees C. to about 45 degrees C. that, such time being sufficient for the Apo AI present in the sample to immunoreact with (immunologically bind) a portion of the anti-Apo AI antibody combining sites present in the monoclonal antibody to form an Apo AI-containing immunoreaction product (immunocomplex). In embodiments where the polypeptide is in the solid phase, the immunocomplex formed is also present in the solid phase.

Biological assay conditions are those that maintain the biological activity of the immunochemical reagents of this invention and the Apo AI sought to be assayed. Those conditions include a temperature range of about 4 degrees C. to about 45 degrees C., a pH value range of about 5 to about 9 and an ionic strength varying from that of distilled water to that of about one molar sodium chloride. Methods for optimizing such conditions are well known in the art.

(c) The amount of Apo AI-containing immunoreaction product that formed in step (b) is determined, thereby determining the amount of Apo AI present in the sample.

Determining the amount of the Apo AI-containing immunoreaction product, either directly or indirectly, can be accomplished by assay techniques well known in the art, and typically depend on the type of indicating means used.

In preferred competitive assay methods, the amount of product determined in step (c) is related to the amount of immunoreaction product similarly formed and determined using a control sample in place of the vascular fluid sample, wherein the control sample contains a known amount of a subject polypeptide from which a standard curve is determined.

Exemplary of the contemplated competitive diagnostic assay, wherein an Apo AI polypeptide is operatively linked to a solid matrix is the ELISA described in Example 9.

In another embodiment, the present invention contemplates a double antibody or "sandwich" immunoassay comprising the steps of:

(a) Forming a first immunoreaction admixture by admixing a vascular fluid sample with a first antibody, preferably a monoclonal antibody, wherein the antibody and Apo AI/HDL present in the sample are capable of forming a first immunoreaction product that can immunoreact with a subject monoclonal antibody. Preferably the first antibody is operatively linked to a solid matrix.

(b) Maintaining the first immunoreaction admixture so formed under biological assay conditions for a time period sufficient to form the first immunoreaction product. Preferably, the first immunoreaction product is then separated from the sample.

(c) Forming a second immunoreaction admixture by admixing the first immunoreaction product with a second antibody, preferably a monoclonal antibody, wherein the second antibody and Apo AI/HDL present in the first immunoreaction product are capable of forming a second immunoreaction product.

(d) Maintaining the second immunoreaction admixture so formed under biological assay conditions for a time period sufficient to form the second or "sandwich" immunoreaction product.

(e) Determining the amount of second immunoreaction product that formed, and thereby the amount of Apo AI in the sample.

Preferably, the subject monoclonal antibody of step (c) is labeled, preferably with an enzyme, and therefore the second immunoreaction product formed is a labeled product.

In one embodiment, the detection of Apo AI polypeptides in a body sample is utilized as a means to monitor the fate of therapeuticallly administered Apo AI polypeptides according to the therapeutic methods disclosed herein.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

F. Therapeutic Compositions

The present invention contemplates therapeutic compositions useful for practicing the therapeutic methods described herein. Therapeutic compositions of the present invention contain a physiologically tolerable carrier together with an Apo AI polypeptide, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

G. Therapeutic Methods

It has been discovered that the Apo AI polypeptides of the present invention have the capacity to modulate the enzymatic activity of lecithin:cholesterol acyltransferase (LCAT) and thereby increase the level of esterified cholesterol in a human patient. The esterification of cholesterol, where it occurs by the activity of LCAT, is referred to herein as "LCAT-mediated cholesterol esterification".

Thus, the present invention provides for a method for increasing esterified cholesterol in a patient comprising administering to the patient a therapeutically effective amount of a physiologically tolerable composition containing an Apo AI polypeptide of the present invention.

A therapeutically effective amount is a predetermined amount calculated to achieve the desired effect, i.e., to increase the amount of esterified cholesterol in a patient. A therapeutically effective amount is typically an amount of an Apo AI polypeptide of the present invention that when administered in a physiologically tolerable composition is sufficient to achieve a plasma concentration of from about 0.1 µg/ml to about 100 µg/ml, preferably from about 1.0 µg/ml to about 50 µml, more preferably at least about 2 µg/ml and usually 5 to 10 µg/ml.

The level of esterified cholesterol present in a patient, particularly in the plasma and associated with lipoprotein particles, can be readily determined by routine clinical analysis. Exemplary assays to monitor the level of esterified cholesterol are described in Example 11. In addition, changes in esterified cholesterol can be monitored during a treatment regimen to determine the effectiveness of the administered Apo AI polypeptide over time.

Thus, the present therapeutic method provides a means for in vivo increasing esterified cholesterol in a human patient displaying symptoms of elevated serum cholesterol, or is otherwise at medical risk by the presence of serum cholesterol, wherein it is beneficial to reduce the levels of cholesterol by cholesterol esterification.

The therapeutic compositions containing an Apo AI polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of an Apo AI polypeptide, a diagnostic method of this invention for detecting an APO AI polypeptide in the subject's blood is useful to characterize the fate of the administered therapeutic composition.

In addition, it has been discovered that Apo AI polypeptides defining a MAB AI-18 epitope as defined in U.S. Pat. No. 5,055,396, filed Nov. 2, 1987 and having Ser. No. 116,248, the teachings ow which patent are hereby incorporated by reference, also have the capacity to modulate LCAT activity and thereby increase the level of esterified cholesterol in a human patient according to the therapeutic methods described herein.

EXAMPLES

The following Examples illustrate, but do not limit, the present invention.
1. Polypeptides Polypeptides AI84-111, AI85-111, AI87-111, AI90-111, AI93-111, AI94-111, AI94-114, AI94-125, AI96-111, AI98-114, AI98-121, AI99-114, AI99-121, AI90-105, AI87-105, and AI95-105 were synthesized using the classical solid-phase technique described by Merrifield, *Adv. Enzymol.,* 32:221–96 (1969) as adapted for use with a Model 430A automated peptide synthesizer (Applied Biosystems, Foster City, Calif.). Polypeptide resins were cleaved by hydrogen fluoride, extracted and analyzed for purity by high-performance liquid chromatograph using a reverse-phase C18 column. (Waters Associates, Milford, Mass.).

The amino acid residue sequence of the polypeptides named above is shown in Table 1.
2. Preparation of Apo AI/HDL HDL was isolated from plasma obtained by plasmaphoresis of normal fasting-donor blood at the local blood bank (San Diego Plasma Center, San Diego, Calif.). For that purpose, plasma so obtained was adjusted to contain a final concentration of 2 millimolar (mM) benzamidine, 14 mM ethylenediaminetetraacetic acid (disodium salt) (EDTA), 20 micrograms per milliliter ($\mu$g/ml) soybean trypsin inhibitor, 10,000 units per ml aprotinin, 20 $\mu$g/ml lima bean trypsin inhibitor, 25 $\mu$g/ml polybrene, and 1$\mu$M D-phenylalanyl-1-prolyl-1-arginine chloromethyl ketone (PPACK). The HDL was then isolated from this adjusted plasma by sequential ultracentrifugation using solid potassium bromide (KBr) for density adjustment.

First, the adjusted plasma was centrifuged at 186,000×g for 18 to 24 hours at 4 degrees centigrade (4° C.). The top layer of the resulting supernatant containing Apo-VLDL was removed and retained. The bottom layer of the supernatant was recovered and admixed with solid KBr layer until the density was greater than 1.063 grams per milliliter (g/ml). The resulting admixture was then layered under a 0.1% EDTA solution containing KEr at density of 1.063 g/ml and centrifuged at 186,000×g for 18 to 24 hours. The bottom layer was again recovered and admixed with solid KBr until the density was adjusted to greater than 1.21 g/ml. That adjusted layer was layered under a 0.1% EDTA solution containing KBr at a density of 1.21 g/ml, and was centrifuged at 186,000×g for more about 48 hours at 4° C.

The resulting top layer was then recovered and admixed with solid KBr until the density was greater than 1.063 g/ml. That adjusted top layer was layered under a 0.1% EDTA solution containing KBr at a density of 1.063 g/ml, and still further centrifuged at 186,000×g for 18 to 24 hours at 4° C.

The middle layer was recovered and admixed with solid KBr until the density was adjusted to greater than 1.21 g/ml. That adjusted middle layer was layered under a 0.1% EDTA solution containing KBr at a density of 1.21 g/ml and centrifuged at 300,000×g for 18 to 24 hours at 4° C. The resulting HDL-containing top layer, having a density equal to 1.063 to 1.21 g/ml, was recovered. The recovered HDL was dialyzed against lipoprotein buffer (LLB; water containing 150 mM NaCl, 0.3 mM EDTA, 0.005% alphatocopherol, and 5 mM benzamidine) and the resulting Apo AI/HDL was stored under sterile conditions for no more than 21 days. The protein concentration of Apo AI/HDL was determined to be between 15 and 25 mg/ml by a modification of the Lowry method [Lowry et al., *J. Biol. Chem.,* 193, 265–275 (1951)] when conducted in the presence of SDS using a bovine serum albumin standard.
3. Preparation of Delipidated Apo AI Delipidated Apo AI was prepared by organically extracting the lipids from Apo AI/HDL. A sample of the Apo AI/HDL prepared in Example 1B was first dialyzed overnight (approximately 18 hours) against 0.01 percent EDTA having a pH value of 7.5, then dialyzed against 0.003 percent EDTA for approximately 6 hours, and subsequently lyophilized at 10 to 20 milligrams of protein per tube. To each tube were admixed 35 ml of absolute ethanol:anhydrous ethyl ether (1:1) at 4° C. Following admixture, the solution was maintained for 20 minutes at −20° C. The solution was then centrifuged for 30 minutes at 1000×g at 0° C., the supernatant was poured off and the Apo AI-containing pellet was retained.

An ethanol ether extraction was performed twice again as described above for a total of three extractions. Subsequently, 35 ml of anhydrous ether at 4° C. were admixed to the sample. The admixture was maintained for 30 minutes at −20° C., centrifuged at 1000×g for 30 minutes at −20° C., and the Apo AI-containing pellet was recovered and dried using nitrogen gas to form delipidated Apo AI. It should be noted that delipidated Apo AI contains not only Apo AI, but also other proteins associated with the HDL, such as Apo AII.

4. Preparation of Isolated Apo AI

Apo AI was isolated from delipidated Apo AI by size fractionation using high pressure liquid chromatography (HPLC) following the procedures of Kinoshita et al., *J. Biochem.*, 94:615–617 (1983). About 300 $\mu$g of delipidated Apo AI prepared in Example 3 was dissolved in 200 microliters ($\mu$l) of 0.1% sodium dodecyl sulfate (SDS), 0.1M sodium phosphate (pH 7.0) and size fractionated on Spherogel-TSK 3000 SW HPLC columns (Beckman Instruments Inc., Fullerton, Calif.). Fractions containing the isolated Apo AI were stored at $-20°$ C.

5. Preparation of Polyclonal Antisera to Synthetic Polypeptides

A. Preparation of Immunogen

LDL is isolated from plasma obtained by plasmaphoresis of normal pooled rabbit blood (Scripps Clinic and Research Foundation Vivarium, La Jolla, Calif.). Plasma so obtained is treated as described for purification of Apo AI/HDL in Example 2. After the second centrifugation, the top layer containing LDL is recovered and the bottom layer containing HDL is discarded. The top layer is admixed with solid KBr until the density is adjusted to greater than 1.063 g/ml. That adjusted layer is layered under a 0.1% EDTA solution containing KBr at a density of 1.21 g/ml and is centrifuged at 186,000×g for 18 to 24 hours at 4° C.

The top layer is then recovered, and solid KBr is admixed until the density is greater than 1.063 g/ml. That adjusted top layer is layered under a 0.1% EDTA solution containing KBr at a density of 1.063 g/ml, and still further centrifuged at 250,000×g for 18 to 24 hours at 4° C. The top layer containing concentrated LDL is recovered and dialyzed against PBS (phosphate-buffered saline, pH 7.2) and stored at $-70°$ C.

The polypeptides AI84-111, AI85-111, AI90-111, AI93-111, AI194-111, AI94-114, AI94-125, AI96-111, A198-114, A1I98-121, AI AI99-114, and AI99-121 are synthesized as described in Example 1. Each polypeptide is individually dissolved in 1.5M sodium acetate, pH 7.8, to a final concentration of 6 mg/ml with a total volume of 5 mls. A dissolved polypeptide is admixed with 2.5 mls each of a 2 mg/ml LDL solution and a 3M sodium acetate solution, pH 7.8, for a peptide:LDL ratio of 1000:1. Added to the polypeptide and LDL reaction mixture is a 500 mM glutaraldehyde solution using a 2.7 molar excess of glutaraldehyde to peptide. The admixture is maintained at room temperature for 10 minutes, after which a 40 mM solution of sodium borohydride is added for a final concentration of 0.2 mM. The admixture is thereafter maintained at 37° C. for 5 to 8 hours, which is followed by dialysis against PBS for 5 days with two buffer changes per day using dialysis tubing having a 12,000 to 14,000 molecular weight cut-off. The dialysed solution is centrifuged at 2500×g for 10 minutes, and the resulting pellet is resuspended in 5 mls PBS to form a peptide-LDL immunogen. A peptide-LDL immunogen is prepared for using each of the above-described peptides in the above immunogen preparation protocol.

B. Immunization and Collection of Polyclonal Antisera

The peptide-LDL immunogen prepared in Example 5A is emulsified using the Ribi Adjuvant System (Ribi Immunochem Research, Inc., Hamilton, Mont.) according to the manufacturer's instructions, and the peptide-LDL antigens are incorporated into the emulsion at a concentration of 300 $\mu$g/ml. Two rabbits are injected with 1 ml of a prepared emulsion after pre-immune serum samples are collected. The 1 ml emulsion dose is administered as follows: 0.30 ml intradermal (0.05 ml in each of 6 sites); 0.40 ml intramuscular (0.2 ml into each hind leg); 0.10 ml subcutaneous (neck region); and 0.20 ml intraperitoneal. The rabbits are injected 6 times at three-week intervals following the injection protocol as detailed. At one week after the second through sixth injections, blood samples are collected to check antibody titer against the specific peptide used as an immunogen by the SPRIA assay described below. The collected blood samples are stirred in a 37° C. oven for 1 hour, after which the samples are centrifuged at 3000×g for 20 minutes. The interface is collected and spun in a microfuge at 12,000×g for 5 minutes. The supernatant containing anti-peptide antibodies is collected and stored at $-20°$ C.

The peptide antibody titers are determined by solid phase radioimmunoassay (SPRIA) essentially as described in Curtiss and Edgington, *J. Biol. Chem.*, 257:15213–15221 (1982). Briefly, 50 $\mu$l of PBS containing 5 $\mu$g/ml synthetic peptides are admixed into the wells of microtiter plates. The plates are maintained overnight (about 16 hours) at 4° C. to permit the peptides to adhere to well walls. After washing the wells four times with SPRIA buffer (2.68 mM KCL, 1.47 mM $KH_2PO_4$, 137 mM NaCl, 8.03 mM $Na_2HPO_4$, 0.05% Tween-20, 0.1 KIU/ml Traysol, 0.1% BSA, 0.015% $NaN_3$), 200 $\mu$l of SPRIA buffer containing 3% normal goat serum (NGS) and 3% bovine serum albumin (BSA) are admixed to each well to block excess protein binding sites. The plates are maintained for 30 minutes at 20° C., the wells emptied by shaking, and blotted dry to form a solid-support, i.e., a solid matrix to which Apo AI/HDL was operatively affixed.

To each well is then admixed 50 $\mu$l of serum sample to form a solid-liquid phase immunoreaction admixture. The admixture is maintained for 2 hours at 37° C. to permit formation of solid-phase immunoreaction products. After washing the wells as previously described, 50 $\mu$l of $^{125}$I-labeled goat anti-mouse IgG at 0.25 $\mu$g protein per ml are admixed to each well to form a labeling reaction admixture. That admixture is maintained for 1 hour at 37° C. to permit formation of $^{125}$I-labeled solid-phase immunoreaction products. After washing the wells as previously described, the amount of $^{125}$I-labeled product bound to each well is determined by gamma scintillation. Specific anti-peptide antibody titers in collected serum samples from immunized rabbits are determined in comparison to pre-immunized normal rabbit serum samples which are a measure of non-specific background. Serum samples are considered to contain anti-peptide polyclonal antibodies if the radioactive signal is 5 times over that seen with normal rabbit serum.

6. Preparation of Monoclonal Antibodies

A. Anti-peptide

The polypeptides designated AI84-111, AI85-111, AI90-111, AI93-111, AI94-111, AI94-114, AI94-125, AI96-111, AI98-114, AI98-121, AI99-114, and AI99-121 are individually prepared as immunogens according to Example 5A. Balb/c ByJ mice (Scripps Clinic and Research Foundation Vivarium, La Jolla, Calif.) are immunized intraperitoneally (i.p.) with 50 $\mu$g of prepared peptide-LDL immunogens in complete Freund's adjuvant (CFA) followed by a second and third immunization using the same peptide-LDL immunogen, each about three weeks apart, in incomplete Freund's adjuvant (IFA). The mice receive a boost of 50 $\mu$g of prepared peptides intravenously (i.v.) in normal saline 4 days prior to fusion and a second similar perfusion boost one day later.

The animals so treated are sacrificed and the spleen of each mouse is harvested. A spleen cell suspension is then prepared. Spleen cells are then extracted from the spleen cell suspension by centrifugation for about 10 minutes at 1000 r.p.m., at 23° C. Following removal of supernatant, the cell pellet is resuspended in 5 ml cold NH$_4$Cl lysing buffer, and was incubated for about 10 minutes.

To the lysed cell suspension are admixed 10 ml Dulbecco's Modified Eagle Medium (DMEM) (GIBCO) and HEPES [4-(2-hydroxyethyl)-1-piperidineethanesulfonic acid] buffer, and that admixture is centrifuged for about 10 minutes at 1000 r.p.m. at 23° C.

The supernatant is decanted, the pellet is resuspended in 15 ml of DMEM and HEPES, and is centrifuged for about 10 minutes at 1000 r.p.m. at 23° C. The above procedure is repeated.

The pellet is then resuspended in 5 ml DMEM and HEPES. An aliquot of the spleen cell suspension is then removed for counting. Fusions are accomplished in the following manner using the non-secreting mouse myeloma cell line P3X63Ag8.653.1, a subclone of line P3x63Ag 8.653 (ATCC 1580). Using a myeloma to spleen cell ratio of about 1 to 10 or about 1 to 5, a sufficient quantity of myeloma cells are centrifuged into a pellet, washed twice in 15 ml DMEM and HEPES, and centrifuged for 10 minutes at 1000 r.p.m. at 23° C.

Spleen cells and myeloma cells are combined in round bottom 15 ml tubes. The cell mixture is centrifuged for 10 minutes at 1000 r.p.m. at 23° C., and the supernatant is removed by aspiration. Thereafter, 200 μl of 50 percent (weight per volume) aqueous polyethylene glycol 4000 molecular weight (PEG; ATCC Baltimore, Md.) at about 37° C. are admixed using a 1 ml pipette with vigorous stirring to disrupt the pellet, and the cells are gently mixed for between 15 and 30 seconds. The cell mixture is centrifuged 4 minutes at 700 r.p.m.

At about 8 minutes for the time of adding the PEG, 5 ml of DMEM plus HEPES buffer are admixed slowly to the pellet, without disturbing the cells. After 1 minute, the resulting admixture is broken up with a 1 ml pipette, and is incubated for an additional 4 minutes. This mixture is centrifuged for 7 minutes at 1000 r.p.m. The supernatant is decanted, 5 ml of HT (hypoxanthine/thymidine) medium are slowly admixed to the pellet, and the admixture is maintained undisturbed for 5 minutes. The pellet is then broken into large chunks, and the final cell suspension is placed into T75 flasks (2.5 ml per flask) into which 7.5 ml HT medium have been placed previously. The resulting cell suspension is incubated at 37° C. to grow the fused cells. After 245 hours 10 ml of HT medium are admixed to the flasks, followed 6 hours later by admixture of 0.3 ml of 0.04 mM aminopterin. 48 hours after fusion, 10 ml of HAT (hypoxanthine/aminopterin/thymidine) medium are admixed to the flasks.

Three days after fusion, viable cells are plated out in 96-well tissue culture plates at about 2×10$^4$ viable cells per well (768 total wells) in HAT buffer medium as described in Kennett et al., *Curr. Top. Microbiol. Immunol.*, 81:77 (1978). The cells are fed seven days after fusion with HAT medium and at approximately 4–5 day intervals thereafter as needed with HT medium. Growth is followed microscopically, and culture supernatants are collected about two weeks later and assayed for the presence of HDL-specific antibody by solid phase radioimmunoassay (RIA) essentially as described in Curtiss and Edgington *J. Biol. Chem.*, 257:15213–15221 (1982).

Briefly, 50 μl of PBS containing 5 μg/ml of the prepared peptide-LDL immunogen is admixed into the wells of microtiter plates. The plates are maintained overnight (about 16 hours) at 4° C. to permit the peptide-LDL immunogen to adhere to well walls. After washing the wells four times with SPRIA buffer (2.68 mM KCl, 1.47 mM KH$_2$PO$_4$, 137 mM NaCl, 8.03 mM Na$_2$HPO$_4$, 0.05% Tween-20, 0.1 KIU/ml Traysol, 0.1% BSA, 0.015% NaN$_3$), 200 μl of SPRIA buffer containing 3% normal goat serum (NGS) and 3% bovine serum albumin (BSA) are admixed to each well to block excess protein binding sites. The plates are maintained for 30 minutes at 20° C., the wells emptied by shaking, and blotted dry to form a solid-support, i.e., a solid matrix to which peptide-LDL immunogen is operatively affixed.

To each well is then admixed 50 μl of hybridoma tissue culture supernatant to form a solid-liquid phase immunoreaction admixture. The admixture is maintained for 2 hours at 37° C. to permit formation of solid-phase immunoreaction products. After washing the wells as previously described, 50 μl of $^{125}$I-labeled goat anti-mouse IgG at 0.25 μg protein per ml are admixed to each well to form a labeling reaction admixture. That admixture is maintained for 1 hour at 37° C. to permit formation of $^{125}$I-labeled solid-phase immunoreaction products. After washing the wells as previously described, the amount of $^{125}$I-labeled product bound to each well is determined by gamma scintillation.

Hybridomas are selected from hybridoma cultures that secrete anti-peptide antibodies into their culture media, and further characterized as described herein.

B. AI-4

The hybridoma that bears the laboratory designation 611 AV63C2.111 and secretes the paratopic molecule designated AI-4 was obtained from a fusion of splenocytes from Balb/c mice (Scripps Clinic and Research Foundation Vivarium, La Jolla, Calif.) immunized with Apo/VLDL as discussed in Example 2. The standard fusion protocol was used as discussed in Example 6. The hybridomas so prepared were screened and assayed as discussed hereinbefore, with the one exception that Apo AI/HDL was used as the coated substrate instead of peptide-LDL immunogen. The hybridoma was deposited on Mar. 5, 1985 with the American Type Culture Collection, Rockville, Md. under the ATCC accession number HB 8744 in accordance with the Budapest Treaty on International Recognition of the Deposit of Microorganisms for the Purposes of Patent Procedure.

C. AI-11

The hybridoma that bears the laboratory designation H103D8.1D11 and secretes the paratopic molecule designated AI-11 was obtained from a fusion of splenocytes from Balb/c mice (Scripps Clinic and Research Foundation Vivarium, La Jolla, Calif.) immunized with Apo AI/HDL as discussed in Example 2. The standard fusion protocol was used as discussed in Example 6. The hybridomas so prepared were screened and assayed as discussed hereinbefore, with the one exception that Apo AI/HDL was used as the coated substrate instead of peptide-LDL immunogen. The hybridoma was deposited on Sep. 16, 1986 with the American Type Culture Collection, Rockville, Md. under the ATCC accession number HB 9201 in accordance with the Budapest Treaty on International Recognition of the Deposit of Microorganisms for the Purposes of Patent Procedure.

D. AI-18

The hybridoma that secrets the paratopic molecule designated AI-18 was obtained as described in U.S. Pat. No. 5,055,396, filed Nov. 2, 1987, and having Ser. No. 116,248, which patent is hereby incorporated by reference. The hybridoma was deposited on 14 Oct. 1987 with the American Type Culture Collection, Rockville, Md. under the ATCC accession number HB9570 in accordance with the Budapest Treaty on International Recognition of the Deposit of Microorganisms for Purposes of Patent Procedure.

E. Monoclonal Antibody Preparation and Purification

Ascites fluids were obtained from separate sets of 10-week old Balb/c mice, which had been primed with 0.3 ml of mineral oil and injected intraperitoneally with 5×10⁶ hybridoma cells with the designations 611 AV63C2.111, H103D8.1D11, and HB9570. The average time for development of ascites was 9 days. Following clarification by centrifugation at 15,000×g for 15 minutes at 23° C., ascites fluids produced by hybridomas were pooled and stored frozen at −20° C.

Purified AI-4, AI-11, and AI-18 monoclonal antibodies from the hybridomas were prepared by fast protein liquid chromatography (FPLC) using a Pharmacia Mono Q HR5/5 anion exchange column (Pharmacia Fine Chemicals, Piscataway, N.J.) using a 0–0.5 molar (M) NaCl gradient in 10 mM Tris, pH 8.0 following directions supplied with the column. Purified Mabs were concentrated using an Amicon stirred ultrafiltration cell (Danvers, Mass.; PM 30 membrane) to a concentration of 1 mg/ml, dialyzed into PBS (phosphate-buffered saline, pH 7.2) and stored at −70° C.

Hybridomas secreting anti-peptide antibodies as described in Example 6A are injected into 10-week old Balb/c mice as described hereinbefore to obtain ascites fluid. Purified anti-peptide monoclonal antibodies are prepared by FPLC as described hereinbefore. Purified Mabs are concentrated in an Amicon stirred ultrafiltration cell and stored as described hereinbefore.

7. Radioiodination

Radioiodination of HDL, Apo AI and immunochemically purified goat anti-mouse Ig was performed enzymatically utilizing the Iodogen iodination procedure and Iodogen obtained from Pierce Biochemicals. The Iodogen iodination was utilized to characterize the antigens and antibodies for the solid phase radioimmunoassay as discussed below.

8. Apo AI-Cyanooen Bromide Fragment Specificity

The Apo AI CNBr fragment specificity of MAB AI-4, MAB AI-11 and MAB AI-18 was determined by Western blot analysis according to the method in Curtiss et al., Proceeding of the Workshop on Lipoprotein Heterogeneity, Ed. by Lippel, NIH Publication No. 87-2646 p. 363–377 (1987). Briefly CNBr fragmentation was performed on isolated Apo AI dissolved in 90% formic acid. CNBr was added in a 13,000 molar excess and the reaction mixture was maintained about 15 hours at about 20 degrees C. Following lyophilization, the resulting CNBr fragments were solubilized in 1% SDS, 0.01M Tris, pH 8.2 and subjected to isoelectric focusing in 6% polyacrylamide slab gels containing 8M urea and 2% ampholine (pH 4 to pH 6) as described by Curtiss et al., *J. Biol. Chem.*, 260:2982–93 (1985). Electrophoretically separated proteins were transferred to nitrocellulose for separate immunoreaction with the monoclonal antibodies. Production of immunoreaction products was detected by radioiodinated goat anti-mouse Ig followed by autoradiography.

The results of these studies indicate that MAB AI-4 does not immunoreact with Apo AI CNBr fragments CNBr1, CNBr2, CNBr3 and CNBr4 but does immunoreact with CNBr2–CNBr3. These CNBr immunoreactant results indicate that MAB AI-4 also immunoreacts with isolated Apo AI.

The results of these studies indicate that MAB AI-11 does not immunoreact with Apo AI CNBr fragments CNBr1, CNBr3 and CNBr4 but does immunoreact with CNBr2. These CNBr immunoreactant results indicate that MAB AI-11 also immunoreacts with isolated Apo AI.

The results of these studies indicate that MAB AI-18 does not immunoreact with Apo AI CNBr fragments CNBr1, CNBr3 and CNBr4 but does immunoreact with CNBR2. These CNBr immunoreactant results indicate that MAB AI-18 also immunoreacts with isolated Apo AI.

9. Solid-Phase Polypeptide ELISA

Apo AI polypeptides AI84-111, AI85-111, AI90-111, AI93-111, AI94-111, AI-94-125, AI96-111, AI99-111, and AI99-114 were tested for immunoreactivity with monoclonal antibody AI-11 in a direct binding ELISA. In the assay, 50 μg/ml of each polypeptide was dissolved in PBS to form a peptide coating solution, of which 150 μl was admixed into the wells of a flexible polyvinyl chloride microtiter plate (Immulon). The wells were then maintained about 16 to 20 at 4° C. to permit the peptide to absorb onto (coat) the walls of the wells. After removing the peptide coating solution by shaking, the wells were washed once with 350 μl of rinsing buffer (PBS containing 1 g/l BSA, 0.5 ml/l Tween 20, and 2 μl/1 aprotinin). Excess protein binding sites were blocked by admixing 200 μl of blocking buffer (PBS containing 3% BSA) into each well, maintaining the wells for 1 hour at 37° C., removing the blocking buffer by shaking, and then washing the wells 3 times as previously described. The plate was then dried for 1 hour at 37° C. followed by addition of 100 μl of PBS containing 0.5 μg/ml horseradish peroxidase conjugated AI-11 antibody to form a solid-liquid phase immunoreaction admixture. The resulting solid-liquid phase immunoreaction admixture was maintained at 20° C. for 1 hour to permit formation of a solid-phase polypeptide-containing immunoreaction product. The wells were then washed 3 times with rinsing buffer to remove unbound antibody.

The amount of immunoreaction product present in the solid phase was then determined by admixing two hundred microliters of OPD substrate into each well to form a developing-reaction admixture. The admixture was maintained for 30 minutes at about 20° C. Subsequently, 50 μl of 4N $H_2SO_4$ were admixed into each well to stop the developing-reaction, and the resulting solution was assayed for absorbance at 450 nanometers using a microtiter plate reader (Dynatech) to detect the amount of formed immunoreaction product.

Apo AI polypeptides AI85-111, AI94-125, and AI96-111 were found to be specifically immunoreactive with the monoclonal antibody AI-11 in the above direct binding ELISA. The Apo AI polypeptides AI90-111, AI93-111 and AI99-114 were also recognized by the antibody but with decreased specificity. The Apo AI polypeptide AI99-111 was not bound by the antibody.

To determine the relative effectiveness of AI-11 binding to Apo AI synthetic polypeptides, a competition ELISA was performed with AI 96-111 as the test synthetic polypeptide in comparison to Apo AI-containing serum and purified Apo AI/HDL. Microtiter plates were coated with AI 96-111 as described hereinbefore. After the drying step of the assay described hereinbefore, 50 μl of a fluid sample (i.e., an Apo AI-containing fluid sample) or standard (i.e., an Apo AI polypeptide) to be assayed were admixed into the polypeptide AI96-111-coated well simultaneously with 50 μl of HRPO-conjugated AI-11 antibody to form an immunoreaction admixture. In the assay described herein, 3 competitors were tested for their ability to compete for binding of AI-11 to the AI 96-111 polypeptide coated over a range of dilutions. The polypeptide AI 96-111 was added in separate coated wells at a starting concentration of 1 mg/ml and diluted 2-fold serially 6 times down to a final concentration of 0.0156 mg/ml. Serum samples as described in Example 2 were added at a starting dilution of 1:10 and diluted 2-fold serially 6 times down to a final dilution of 1:320. Apo AI/HDL as described in Example 2 was added at a starting concentration of 1 mg/ml and diluted 2-fold 5 times down to a final concentration of 0.031 mg/ml. The plate was then incubated for 30 minutes at room temperature. The plate was washed and the assay developed as described hereinbefore to determine the amount of immunoreaction product formed, and thereby the amount of competitor present in the added fluid sample.

The results of this assay, shown in FIG. 2, indicate that MAB AI-11 immunoreacts with AI96-111 present in the fluid sample but has a greater affinity for native Apo AI in serum and purified HDL.

10. MAB AI-4, AI-11, and AI-18 Immunoreactivity

A. MAB AI-4

The immunoreactivity of MAB AI-4 for native Apo AI/HDL and various synthetic polypeptides was examined by a competitive RIA performed as follows:

One hundred μl of PBS (0.15M NaCl, 0.01M NaPO$_4$, pH 7.2) containing 10 μg/ml Apo AI/HDL were admixed to the wells of microtiter plates. The plates were maintained for 1 hour at 20° C. on a rotating platform to allow the Apo AI/HDL to adhere to the wells and form solid supports. After aspirating excess liquid from the wells, 200 μl of block solution (3% BSA, 3% NGS in PBS) was admixed to each well, and the wells were maintained for 30 minutes at 20° C. on a rotating platform. Subsequently, the blocking solution was removed by aspiration, and the wells were washed 3 times with SPRIA buffer.

To each well was then admixed first with 50 μl of PBS containing 3% BSA and various concentrations of competitor antigen, i.e., Apo AI/HDL peptide, and, second, 50 μl of MAB AI-4 in the form of clarified ascites diluted 1:11.25× 10$^5$ in PBS containing 3% BSA to form competitive immunoreaction admixtures. In control wells, either competing antigen or antibody was replaced by PBS containing 3% BSA.

The immunoreaction admixtures were maintained about 16 hours at 4° C. on a rotating platform to permit formation of solid-phase immunoreaction products. After washing the wells as previously described, 100 μl of $^{125}$I-labeled goat anti-mouse Ig ($^{125}$I-goat anti-mouse Ig diluted to 2×10$^5$ trichloracetic acid precipitable disintegrations per minute per 100 μl in PBS containing 3% BSA) were admixed to each well. The labeling immunoreaction admixtures so formed were maintained for 4 hours at 4° C. on a rotating platform. Subsequently, the wells were washed with SPRIA buffer as previously described, and the amount of $^{125}$I-labeled solid-phase immunoreaction product formed was determined in a gamma counter.

The ability of MAB AI-4 to immunoreact with Apo AI/HDL was compared by using Apo AI/HDL and various synthetic peptides as competitors in the above-described RIA. The results of this study are shown in FIG. 3. B/Bo represents corrected CPMs which are plotted against increasing concentrations of competition in μg/ml. B/Bo values are determined in the following formula:

$$\frac{(\text{Competitor Sample } CPM - 0\% \, CPM)}{(100\% \, CPM - 0\% \, CPM)}$$

where 0% CPM is a measure of non-specific background based on CPM obtained in RIAs where wells coated with Apo AI/HDL are reacted with the labeled secondary antibody in the absence of primary antibody and competitor, and where 100% CPM is a measure of the maximum non-competed binding of primary antibody to the substrate coated to the wells. The more efficiently a competitor binds to the primary antibody, the lower the B/Bo values. The results of the assay in FIG. 3 show that peptide AI94-125 is a better competitor of AI-4 MAB binding to Apo AI/HDL-coated wells than is peptide AI99-121 or Apo AI/HDL itself.

Peptides AI90-111, AI93-111, and AI96-111 are ineffective in the competition assay, thus are not immunoreactive with AI-4 MAB.

Other peptides were evaluated for their ability to immunoreact with AI-4 MAB in competitive RIAs described herein. Peptides AI94-114 and AI99-114 exhibited partial reactivity. Peptides AI79-95, AI68-105, AI74-105, AI87-105, AI87-111, AI90-105, AI93-101, AI95-105, AI96-101, AI100-105, AI101-111, AI105-116 and AI115-126 did not react with AI-4 MAB.

Apo AI polypeptides immunoreactive with MAB AI-4 according to the above competition RIA are summarized in FIG. 4. The conserved native epitope defined by MAB AI-4 includes the amino acid residues at positions 99-114 at a minimum, because peptide AI99-114 immunoreacted with MAB AI-4. However, peptide AI99-121 immunoreacted with MAB AI-4 nearly as well as Apo AI/HDL, indicating that the residues 99-121 define a preferred epitope on Apo AI. A particularly preferred polypeptide for use in diagnostic competition ELISA or RIA is peptide AI94-125.

Peptide AI99-121 was prepared having an E in residue position 104 in place of the usual residue F and was shown to immunoreact with MAB AI-4. Thus, Apo AI peptides defined by MAB AI-4 that have either an E or an F residue at position 104 will immunoreact with MAB AI-4 and are useful in diagnostic methods when used in conjunction with MAB AI-4.

B. MAB AI-11

The immunoreactivity of MAB AI-11 for native Apo AI/HDL and various synthetic polypeptides was examined by a competitive RIA as described in Example 10A. The results of these assays are shown in FIG. 5. Peptides AI96-111, AI90-111, and AI93-111 are competitive inhibitors of AI-11 MAB binding to Apo AI/HDL but are less effective than the native protein itself. The peptide AI99-121 does not bind to the AI-11 MAB. Other peptides were evaluated for their ability to immunoreact with AI-11 MAE in competitive RIAs described herein. Peptides AI84-111, AI94-111 and AI94-125 were tested in the above competitive RIA and also inhibited the immunoreactivity of MAB AI-11 with Apo AI/HDL. Peptides AI79-95, AI87-105, AI87-111 (with an E instead of an F residue at position 104), AI90-105, AI93-101, AI95-105, AI96-101, AI99-121, AI100-105, AI105-116, and AI115-126 do not immunoreact with AI-11 MAB.

Apo AI polypeptides immunoreactive with MAB AI-11 according to the above competition RIA are summarized in FIG. 6. The conserved native epitope defined by MAB AI-11 includes the amino acid residues at positions 96–111, because peptide AI96-111 immunoreacted with MAB AI-11

C. MAB AI-18

As described in U.S. Pat. No. 5,055,396, filed Nov. 2, 1987 and having Ser. No. 116,248, the immunoreactivity of MAB AI-18 for native Apo AI/HDL and various synthetic polypeptides was examined by a competitive RIA, performed as described in Example 10A. The results indicate that MAB AI-18 displays equivalent immunoreactivites for peptides AI90-105, AI90-111, AI87-105, and AI95-105. In addition, a comparison of the immunoreactivity of MAB AI-18 for AI95-105, AI95-105 (-P) and AI95-105 (G/P) indicate that the presence of proline at position 99 is required for expression by a peptide of the conserved Apo AI-epitope recognized by MAB AI-18.

11. Inhibition of LCAT-Mediated Cholesterol Esterification by Apo AI Specific Antibodies A. Antibody mediated inhibition Proteoliposomes containing lecithin, 14-C-cholesterol and Apo AI were prepared in the following manner. 7.7 mg of phosphatidylcholine (egg yolk lecithin) were dried under nitrogen gas in a 13×100 glass test tube. 116 μg of cholesterol from a 1 mg/ml solution in ethanol and 78.3 μg of 14-C-cholesterol from a 0.29 mg/ml solution in benzene with a specific activity of 0.04 mCi/ml were dried in the same tube without coming in contact with the dried lecithin. To this tube was added 0.3 ml of a 725 mM solution of sodium cholate in Tris HCl buffer (10 mM Tris, 140 mM NaCl, 1 mM EDTA-tetrasodium salt, pH 7.2), 2.5 ml Tris HCl buffer and 0.8 ml of a 1 mg/ml solution of purified Apo AI in Tris HCl buffer. The admixture was vortexed for 60 seconds and then mixed on a rotating wheel at room temperature for 1 hour. The admixture was dialyzed overnight against 500 ml of Tris HCl buffer which was changed 5 times. The proteoliposomes were adjusted to a volume of 4 ml after dialysis and stored in the refrigerator. The 4 mls of proteoliposomes contained $9.78 \times 10^{-6}$ mole lecithin, $3.0 \times 10^{-7}$ mole cholesterol, $2.01 \times 10^{-7}$ mole 14-C-cholesterol and $3.14 \times 10^{-8}$ mole Apo AI. Molar ratios of lecithin:cholesterol:Apo AI were 250:12.5:0.8.

The LCAT-mediated cholesterol esterification assay, and including inhibition of esterification using anti-Apo AI antibodies, was performed in duplicate. To glass screw-cap tubes was added 100 μl of the prepared proteoliposome solution, 125 μl of a 2% solution of human serum albumin in Tris HCl buffer, monoclonal antibodies in amounts from 15.6 μg to 500 μg/tube and Tris HCl buffer to a final volume of 455 μl. The tubes were capped, vortexed and maintained for 30 minutes in a 37° C. water bath. To the tubes was added 25 μl of a 100 mM solution of mercaptoethanol in Tris HCl buffer and 30 μl of lipoprotein depleted plasma (LPDP) as the source of LCAT. The tubes were again capped, vortexed and maintained for 1 hour in a 37° C. water bath, after which time the enzyme reaction was stopped by addition of 2 ml of ethanol. Controls for the assay included duplicate tubes without LPDP and duplicate tubes with LPDP, but no antibody which will result in 100% esterification.

Cholesterol and cholesterol esters were extracted from the reaction by adding to each tube 5 ml hexane containing 16 μg/ml cholesterol and 16 μg/ml cholesteryl linoleate. The admixture was vortexed for 20 seconds, and the upper layer was removed to a 13×100 glass tube. To the original reaction mixture was added 3 ml more of the hexane/cholesterol/cholesteryl linoleate solution. This admixture was vortexed, and the upper layer was removed and added to the first extraction. The contents of both extractions were dried under nitrogen gas or evaporated overnight.

The dried contents of the tubes containing the extracted material was dissolved in 50 μl of chloroform and spotted onto Empore thin layer chromatography sheets (TLC). The tube was rinsed with an additional 50 μl and added to the first spot. The TLC sheets were developed in a solvent of hexane:ethyl ether in a 60:40 ratio. The sheets were air dried and exposed to iodine to visualize the origins. The sheets were then placed on Kodak X-OMAT autoradiography for an overnight exposure. Areas on the TLC sheets corresponding to radioactive signals on the film were cut and placed in scintillation vials with 3 ml of scintillant (PPD-PDPDP in toluene). The 14-C radioactive label was detected in a beta counter. Fractional esterification rates (FER) were determined from the scintillation counts where FER is expressed as cholesteryl ester cpm over cholesterol plus cholesteryl ester cpm.

The results of LCAT-mediated cholesterol esterification assays in which five monoclonal antibodies, AI-4, AI-9, AI-11, AI-16 and AI-18, were tested for their ability to inhibit cholesterol esterification is shown in FIG. 7. Purified MABs AI-4 and AI-11 were prepared as described in Example 6C. Purified MABs AI-9, AI-16 and AI-18 were generated from fusions of splenocytes from mice immunized with Apo AI/HDL similarly to the methods described in Example 6C. The MABs AI-9 and AI-16 were used as control MABs in the LCAT-mediated cholesterol esterification assay and are known to immunoreact with CNBr4 and the Apo AI amino acid residues sequence AI1-15, respectively. The MAB AI-18 immunoreacts with the Apo AI amino acid residue sequence AI95-105.

In this assay, 250 μg of each antibody was evaluated. At this amount, the antibodies and Apo AI were in equal molar concentrations. Data for each monoclonal antibody is expressed as percent of control where control is the FER in the absence of antibody but in the presence of LPDP. The control FERs for the results range from 0.0626 to 0.0948 per hour. Each bar represents data from two experiments, and each experiment is done in duplicate. Monoclonal antibody AI-11 was the most effective inhibitor of cholesterol esterification followed by AI-4. Monoclonal antibodies AI-16 and AI-18 inhibited esterification by an equal amount. Monoclonal AI-9 was ineffective at blocking cholesterol esterification.

B. Correlation Between Inhibition of LCAT-Mediated Cholesterol Esterification and Antibody Binding to Apo AI To determine if the degree of antibody inhibition of LCAT-mediated cholesterol esterification was a reflection of the degree to which each antibody could bind to apo A-I in the proteoliposomes, we examined the extent of antibody binding. This was measured in double antibody fluid phase radioimmunoassays using radiolabeled proteoliposomes that had the same composition as those used in the LCAT activation assay (Example 11.A).

The fluid phase immunoassays were designed to reproduce the conditions of antibody/antigen interaction in the LCAT assay. Proteoliposomes that contained 48 μg/ml of Apo A-I and approximately 300,000 cpm/tube were incubated with a 4-fold molar excess of each antibody and 1% HSA for 30 minutes at 37° C. Mercaptoethanol and LPDP were added for a further 1 hour incubation at 37° C. The extent of antibody binding was assessed following precipitation by an additional incubation with 2 ml of Tachisorb M (Calbiochem, La Jolla, Calif.) for 60 min. at room temperature on a platform shaker. The tubes were then centrifuged at 1500×g for 20 min. Supernatants were aspirated and the pellets were washed with 1 ml of cold PBS and recentrifuged. The radioactivity in the pellets was counted in an Iso-Data 20/20 series gamma counter. Non-specific binding was assessed in samples exposed only to Tachisorb M and was in all cases less than 10%. Data were expressed as the ratio B/Bo, where Bo is the TCA precipitable cpm (90–100% of total cpm) less non-specific binding and B is the cpm bound in the presence of antibody less non-specific binding. The data is provided in FIG. 8.

In FIG. 8 the extent of binding of proteoliposomes by a 4-fold molar excess of antibody under conditions exactly simulating those of the LCAT assay (represented as B/Bo) is compared with the extent of inhibition of LCAT activation by a 4-fold molar excess of antibody (represented as % inhibition). A direct relationship between the degree of binding and the degree of LCAT inhibition was evident with antibodies AI-11, AI-4 and AI-18. However, this relationship was not observed with antibodies AI-16, AI-9 and AI-10, where antibody binding to proteoliposomes was significantly greater than the inhibition of LCAT-mediated cholesterol esterification. The results indicated that antibody inhibition of Apo AI-activation of LCAT was specific for some but not all antibodies, namely, AI-4, AI-11 and AI-18. Interestingly, for antibodies AI-11, AI-4 and AI-18, LCAT inhibition was significantly greater than binding to the proteoliposomes.

Collectively, these data show that the Apo AI epitopes recognized by MAB AI-4 and MAB AI-18, and particularly by MAB AI-11 comprise a part of the Apo AI molecule that is involved in the process by which Apo AI normally increases esterification of cholesterol. Thus, polypeptides which immunologically mimic the epitope defined by MAB AI-4, MAB AI-18, or MAB AI-11 represent useful Apo AI polypeptides that will function as an analog of Apo AI in the capacity of Apo AI to increase esterification of cholesterol. That is, Apo AI polypeptides of this invention can be used similarly to Apo AI itself to increase cholesterol esterification.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A diagnostic system, in kit form, comprising, in an amount sufficient to perform at least one assay, a monoclonal antibody that immunoreacts with:
   (a) Apo AI/HDL,
   (b) isolated Apo AI,
   (c) Apo AI CNBr2, and
   (d) the polypeptide KVQPYLDDFQKKWQEE, (SEQ ID NO 1:12–27), but do not immunoreact with:
   (e) Apo AI CNBr1,
   (f) Apo AI CNBr3, and
   (g) the polypeptide SKDLEEVKAKVQPYLDDE-QKKWQEE (SEQ ID NO 4:1–25),
   (h) the polypeptide SKDLEEVKAKVQPYLDDFQ (SEQ ID NO 1:3–21), and
   (i) the polypeptide PYLDDFQKKWQEEME-LYRQKVEP (SEQ ID NO 1:15–37); and an Apo AI polypeptide comprising no more than 60 amino acid residues and including an amino acid residue sequence represented by the formula (SEQ ID NO 1:12–27): -KVQPYLDDFQKKWQEE-, wherein said polypeptide is free of homoserine lactone.

2. The diagnostic system of claim 1 wherein said antibody is operatively linked to an enzyme indicating means.

3. The diagnostic system of claim 1 wherein said antibody is produced by the hybridoma having ATCC designation HB9201.

4. The diagnostic system of claim 1 wherein said APO AI polypeptide has an amino acid residue sequence represented by a formula selected from the group consisting of:
QEMSKDLEEVKAKVQPYLDDFQKKWQEE,
EMSKDLEEVKAKVQPYLDDFQKKWQEE,
LEEVKAKVQPYLDDFQKKWQEE,
VKAKVQPYLDDFQKKWQEE,
KAKVQPYLDDFQKKWQEE,
KAKVQPYLDDFQKKWQEEMELYRQKVEPLRAE, and
KVQPYLDDFQKKWQEE, respectively, SEQ ID NOS 2:2–29, 1:1–27, 1:6–27, 1:9–27, 1:10–27, 1:10–41 and 1:12–27.

5. The diagnostic system of claim 1 wherein said APO AI polypeptide is operatively linked to a solid matrix.

6. A method of assaying the amount of Apo AI in a vascular fluid sample comprising the steps of:
   (a) forming an immunoreaction admixture by admixing a vascular fluid sample with:
      (I) an anti-Apo AI monoclonal antibody that immunoreacts with:
         (1) Apo AI/HDL,
         (2) isolated Apo AI,
         (3) Apo AI CNBr2, and
         (4) the polypeptide KVQPYLDDFQKKWQEE (SEQ ID NO 1:12–27) but do not immunoreact with:
         (5) Apo AI CNBr1,
         (6) Apo AI CNBr3,
         (7) the polypeptide SKDLEEVKAKVQPYLDDE-QKKWQEE (SEQ ID NO 4:1–25),
         (8) the polypeptide SKDLEEVKAKVQPYLDDFQ (SEQ ID NO 1:3–21), and
         (9) the polypeptide PYLDDFQKKWQEEME-LYRQKVEP (SEQ ID NO 1:15–37); and
      (II) an Apo AI polypeptide comprising no more than 60 amino acid residues and including an amino acid residue sequence represented by the formula (SEQ ID NO 1:12–27): -KVQPYLDDFQKKWQEE-, said polypeptide being operatively linked to a solid matrix such that the immunoreaction admixture has both a liquid phase and a solid phase;

(b) maintaining said immunoreaction admixture for a time period sufficient to form an Apo AI-containing immunoreaction product in the solid phase, and (c) determining the amount of product formed in step (b), thereby determining the amount of said Apo AI in said vascular fluid sample.

7. The method of claim 6 wherein said Apo AI polypeptide has an amino acid residue sequence represented by a formula selected from the group consisting of:
QEMSKDLEEVKAKVQPYLDDFQKKWQEE,
EMSKDLEEVKAKVQPYLDDFQKKWQEE,
LEEVKAKVQPYLDDFQKKWQEE,
VKAKVQPYLDDFQKKWQEE,
KAKVQPYLDDFQKKWQEE,
KAKVQPYLDDFQKKWQEEMELYRQKVEPLRAE, and
KVQPYLDDFQKKWQEE, respectively, SEQ ID NOS 2:2–29, 1:1–27, 1:6–27, 1:9–27, 1:10–27, 1:10–41 and 1:12–27.

8. The method of claim 6 wherein said antibody is operatively linked to an enzyme label, and said product formed in step (b) is a labeled immunoreaction product.

9. The method of claim 6 wherein said antibody is produced by the hybridoma having ATCC designation HB9201.

10. A diagnostic system, in kit form, comprising, in an amount sufficient to perform at least one assay, a monoclonal antibody that immunoreacts with:

(a) Apo AI/HDL, (b) isolated Apo AI, (c) Apo AI CNBr2-CNBr3, and (d) the polypeptide PYLDDFQKKWQEEMEL (SEQ ID NO 1:15–30), but do not immunoreact with:

(e) Apo AI CNBr1, (f) the polypeptide SKDLEEVKAKVQPYLDDFQKKWQEE (SEQ ID NO 1:3–27).

(g) the polypeptide LEEVKAKVQPYLDDFQKKWQEE (SEQ ID NO 1:6–27), and (h) the polypeptide YRQKVEPLRAEL (SEQ ID NO 1:31–42); and an Apo AI polypeptide comprising no more than about 60 amino acid residues and including an amino acid residue sequence represented by the formula (SEQ ID NO 3:6–21):
-PYLDDXQKKWQEEMEL-, wherein X is either E or F.

11. The diagnostic system of claim 10 wherein said antibody is operatively linked to an enzyme indicating means.

12. The diagnostic system of claim 10 wherein said antibody is produced by the hybridoma having ATCC designation HB8744.

13. The diagnostic system of claim 10 wherein said APO AI polypeptide has an amino acid residue sequence represented by a formula selected from the group consisting of:
KAKVQPYLDDXQKKWQEEMEL,
KAKVQPYLDDXQKKWQEEMELYRQKVEPLRAE,
QPYLDDXQKKWQEEMEL,
QPYLDDXQKKWQEEMELYRQKVEP,
PYLDDXQKKWQEEMEL, and
PYLDDXQKKWQEEMELYRQKVEP, respectively, SEQ ID NOS 3:1–21, 3:1–32, 3:5–21, 3:5–28, 3:6–21 and 3:6–28.

14. The diagnostic system of claim 10 wherein said APO AI polypeptide is operatively linked to a solid matrix.

15. A method of assaying the amount of Apo AI in a vascular fluid sample comprising the steps of:

(a) forming an immunoreaction admixture by admixing a vascular fluid sample with:

(I) an anti-Apo AI monoclonal antibody that immunoreacts with:

(1) Apo AI/HDL, (2) isolated Apo AI, (3) Apo AI CNBr2–CNBr3, and (4) the polypeptide PYLDDFQKKWQEEMEL (SEQ ID NO 1:15–30), but do not immunoreact with:

(5) Apo AI CNBr1, (6) the polypeptide SKDLEEVKAKVQPYLDDFQKKWQEE (SEQ ID NO 1:3–27), (7) the polypeptide LEEVKAKVQPYLDDFQKKWQEE (SEQ ID NO 1:6–27), and (8) the polypeptide YRQKVEPLRAEL (SEQ ID NO 1:31–42);

(II) an Apo AI polypeptide comprising no more than about 60 amino acid residues and including an amino acid residue sequence represented by the formula (SEQ ID NO 3:6–21):
-PYLDDXQKKWQEEMEL-, wherein X is either E or F, said polypeptide being operatively linked to a solid support such that the immunoreaction admixture has both a liquid phase and a solid phase;

(b) maintaining said immunoreaction admixture for a time period sufficient to form an Apo AI-containing immunoreaction product in the solid phase, and (c) determining the amount of product formed in step (b), thereby determining the amount of said Apo AI in said vascular fluid sample.

16. The method of claim 15 wherein said Apo AI polypeptide has an amino acid residue sequence represented by a formula selected from the group consisting of:
KAKVQPYLDDXQKKWQEEMEL,
KAKVQPYLDDXQKKWQEEMELYRQKVEPLRAE,
QPYLDDXQKKWQEEMEL,
QPYLDDXQKKWQEEMELYRQKVEP,
PYLDDXQKKWQEEMEL, and
PYLDDXQKKWQEEMELYRQKVEP,
respectively SEQ ID NOS 3:1–21, 3:1–32, 3:5–21, 3:5–28, 3:6–21 and 3:6–28.

17. The method of claim 15 wherein said antibody is operatively linked to an enzyme label, and said product formed in step (b) is a labeled immunoreaction product.

18. The method of claim 15 wherein said antibody is produced by the hybridoma having ATCC designation HB8744.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 64 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:1:

Glu Met Ser Lys Asp Leu Glu Glu Val Lys Ala Lys Val Gln Pro Tyr
1               5                   10                  15
Leu Asp Asp Phe Gln Lys Lys Trp Gln Glu Glu Met Glu Leu Tyr Arg
                20                  25                  30
Gln Lys Val Glu Pro Leu Arg Ala Glu Leu Gln Glu Gly Ala Arg Gln
            35                  40                  45
Lys Leu His Glu Leu Gln Glu Lys Leu Ser Pro Leu Gly Glu Glu Met
        50                  55                  60

( 2 ) INFORMATION FOR SEQ ID NO:2:

( i ) SEQUENCE CHARACTERISTICS:
( A ) LENGTH: 44 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:2:

Arg Gln Glu Met Ser Lys Asp Leu Glu Glu Val Lys Ala Lys Val Gln
1               5                   10                  15
Pro Tyr Leu Asp Asp Phe Gln Lys Lys Trp Gln Glu Glu Met Glu Leu
                20                  25                  30
Tyr Arg Gln Lys Val Glu Pro Leu Arg Ala Glu Leu
            35                  40

( 2 ) INFORMATION FOR SEQ ID NO:3:

( i ) SEQUENCE CHARACTERISTICS:
( A ) LENGTH: 32 amino acids
( B ) TYPE: amino acid
( D ) TOPOLOGY: linear ( i i ) MOLECULE TYPE: peptide (v) FRAGMENT TYPE: internal (ix) FEATURE:
(A) NAME/KEY: Region
(B) LOCATION: 11
(D) OTHER INFORMATION: /note= "Xaa can be either E (Glu) or F (Phe)"

(xi) SEQUENCE DESCRIPTION: SEQ ID NO:3:

Lys Ala Lys Val Gln Pro Tyr Leu Asp Asp Xaa Gln Lys Lys Trp Gln
1               5                   10                  15

Glu Glu Met Glu Leu Tyr Arg Gln Lys Val Glu Pro Leu Arg Ala Glu
            20                  25                  30

(2) INFORMATION FOR SEQ ID NO:4:

(i) SEQUENCE CHARACTERISTICS:
(A) LENGTH: 25 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:4:

Ser Lys Asp Leu Glu Glu Val Lys Ala Lys Val Gln Pro Tyr Leu Asp
1               5                   10                  15

Asp Glu Gln Lys Lys Trp Gln Glu Glu
            20                  25